(12) United States Patent
McCarthy et al.

(10) Patent No.: US 8,668,924 B2
(45) Date of Patent: Mar. 11, 2014

(54) WOUND DRESSING AND METHOD FOR CONTROLLING SEVERE, LIFE-THREATENING BLEEDING

(75) Inventors: Simon J. McCarthy, Portland, OR (US); Kenton W. Gregory, Portland, OR (US); William P. Wiesmann, Washington, DC (US); Todd D. Campbell, Petaluma, CA (US)

(73) Assignees: Providence Health System—Oregon, Renton, WA (US); Kenton W. Gregory, Portland, OR (US)

(*) Notice: Subject to any disclaimer, the term of this patent is extended or adjusted under 35 U.S.C. 154(b) by 495 days.

(21) Appl. No.: 12/925,292

(22) Filed: Oct. 18, 2010

(65) Prior Publication Data

US 2011/0034410 A1   Feb. 10, 2011

Related U.S. Application Data

(60) Continuation of application No. 12/148,320, filed on Apr. 18, 2008, now abandoned, which is a division of application No. 10/743,052, filed on Dec. 23, 2003, now Pat. No. 7,371,403, which is a continuation-in-part of application No. 10/480,827, filed as application No. PCT/US02/18757 on Jun. 14, 2002, now Pat. No. 7,482,503.

(51) Int. Cl.
| | |
|---|---|
| *A61F 13/02* | (2006.01) |
| *A61L 15/00* | (2006.01) |
| *C08B 37/08* | (2006.01) |
| *A61F 13/00* | (2006.01) |
| *C08L 1/00* | (2006.01) |
| *A61L 15/28* | (2006.01) |
| *A61L 15/42* | (2006.01) |

(52) U.S. Cl.
CPC ......... *A61F 13/0203* (2013.01); *A61F 13/0289* (2013.01); *A61F 13/0253* (2013.01); *A61F 2013/00463* (2013.01); *A61F 2013/00468* (2013.01); *C08L 1/00* (2013.01); *A61L 15/28* (2013.01); *A61L 15/425* (2013.01); *A61L 2400/04* (2013.01); *A61F 13/0276* (2013.01); *A61F 2013/0072* (2013.01); *A61F 2013/00931* (2013.01)
USPC ................ 424/445; 514/55; 536/20

(58) Field of Classification Search
None
See application file for complete search history.

(56) References Cited

U.S. PATENT DOCUMENTS

| | | |
|---|---|---|
| 2,610,625 A | 9/1952 | Sifferd et al. |
| 2,858,830 A | 11/1958 | Robins |
| 2,923,664 A | 2/1960 | Cook et al. |
| 3,551,556 A | 12/1970 | Kliment et al. |
| 3,632,754 A | 1/1972 | Balassa |
| 3,800,792 A | 4/1974 | McKnight et al. |
| 3,801,675 A | 4/1974 | Russell |
| 3,849,238 A | 11/1974 | Gould et al. |
| 3,902,497 A | 9/1975 | Casey |
| 3,911,116 A | 10/1975 | Balassa |
| 3,954,493 A | 5/1976 | Battista et al. |
| 3,977,406 A | 8/1976 | Roth |
| 4,040,884 A | 8/1977 | Roth |
| 4,056,103 A | 11/1977 | Kaczmarzyk et al. |
| 4,068,757 A | 1/1978 | Casey |
| 4,094,743 A | 6/1978 | Leuba |
| 4,195,175 A | 3/1980 | Peniston et al. |
| 4,292,972 A | 10/1981 | Palwelchak et al. |
| 4,373,519 A | 2/1983 | Errede et al. |
| 4,394,373 A | 7/1983 | Malette et al. |
| 4,452,785 A | 6/1984 | Malette et al. |
| 4,460,642 A | 7/1984 | Errede et al. |
| 4,501,835 A | 2/1985 | Berke |
| 4,524,064 A | 6/1985 | Nambu |
| 4,532,134 A | 7/1985 | Malette et al. |
| 4,533,326 A | 8/1985 | Anthony |
| 4,541,426 A | 9/1985 | Webster |
| 4,599,209 A | 7/1986 | Dautzenberg et al. |
| 4,651,725 A | 3/1987 | Kifune et al. |
| 4,684,370 A | 8/1987 | Barrett |

(Continued)

FOREIGN PATENT DOCUMENTS

| | | |
|---|---|---|
| EP | 0 353 972 | 2/1990 |
| EP | 0477979 | 9/1991 |

(Continued)

OTHER PUBLICATIONS

Schoof et al., Journal of Biomedical Material Research, 58: 352-357 (2001).*

(Continued)

*Primary Examiner* — Kortney L Klinkel
*Assistant Examiner* — Lisbeth C Robinson
(74) *Attorney, Agent, or Firm* — Miller Nash LLP

(57) ABSTRACT

This invention is directed to advanced hemorrhage control wound dressings, and methods of using and producing same. The subject wound dressing is constructed from a non-mammalian material for control of severe 5 bleeding. The wound dressing for controlling severe bleeding is formed of a biomaterial comprising chitosan, a hydrophilic polymer, a polyacrylic polymer or a combination thereof, The kind of severe, life-threatening bleeding contemplated by this invention is typically of the type not capable of being stanched when a conventional gauze wound dressing is applied with conventional 10 pressure to the subject wound. The wound dressing being capable of substantially stanching the flow of the severe life-threatening bleeding from the wound by adhering to the wound site, to seal the wound, to accelerate blood clot formation at the wound site, to reinforce clot formation at the wound site and prevent bleed out from the wound site, and to substantially prohibit the flow of 15 blood out of the wound site.

19 Claims, 18 Drawing Sheets

(56) References Cited

U.S. PATENT DOCUMENTS

| | | | |
|---|---|---|---|
| 4,699,135 A | 10/1987 | Motosugi et al. | |
| 4,759,348 A | 7/1988 | Cawood | |
| 4,772,419 A | 9/1988 | Malson et al. | |
| 4,833,237 A | 5/1989 | Kawamura et al. | |
| 4,948,540 A | 8/1990 | Nigam | |
| 4,952,618 A | 8/1990 | Olsen | |
| 4,958,011 A | 9/1990 | Bade | |
| 4,960,413 A | 10/1990 | Sagar et al. | |
| 4,973,493 A | 11/1990 | Guire | |
| 4,977,892 A | 12/1990 | Ewall | |
| 5,006,071 A | 4/1991 | Carter | |
| 5,024,841 A * | 6/1991 | Chu et al. | 424/422 |
| 5,035,893 A | 7/1991 | Shioya et al. | |
| 5,062,418 A | 11/1991 | Dyer et al. | |
| 5,116,824 A | 5/1992 | Miyata et al. | |
| 5,154,928 A | 10/1992 | Andrews | |
| 5,206,028 A * | 4/1993 | Li | 424/484 |
| 5,254,301 A | 10/1993 | Sessions et al. | |
| 5,300,494 A | 4/1994 | Brode, II et al. | |
| 5,376,376 A | 12/1994 | Li | |
| 5,378,472 A | 1/1995 | Muzzarelli | |
| 5,420,197 A | 5/1995 | Lorenz et al. | |
| 5,454,719 A | 10/1995 | Hamblen | |
| 5,525,710 A | 6/1996 | Unger et al. | |
| 5,597,581 A | 1/1997 | Kaessmann et al. | |
| 5,643,596 A * | 7/1997 | Pruss et al. | 424/426 |
| 5,700,476 A | 12/1997 | Rosenthal et al. | |
| 5,756,111 A | 5/1998 | Yoshikawa et al. | |
| 5,797,960 A | 8/1998 | Stevens et al. | |
| 5,821,271 A | 10/1998 | Roenigk | |
| 5,827,265 A | 10/1998 | Glinsky et al. | |
| 5,836,970 A * | 11/1998 | Pandit | 606/213 |
| 5,840,777 A | 11/1998 | Eagles et al. | |
| 5,858,292 A | 1/1999 | Dragoo et al. | |
| 5,858,350 A | 1/1999 | Vournakis et al. | |
| 5,952,618 A | 9/1999 | Deslauriers | |
| 5,961,478 A | 10/1999 | Timmermans | |
| 6,054,122 A | 4/2000 | MacPhee et al. | |
| 6,103,369 A | 8/2000 | Lucast et al. | |
| 6,124,273 A | 9/2000 | Drohan et al. | |
| 6,156,330 A | 12/2000 | Tsukada et al. | |
| 6,162,241 A | 12/2000 | Coury et al. | |
| 6,225,521 B1 | 5/2001 | Gueret | |
| 6,270,515 B1 | 8/2001 | Linden et al. | |
| 6,406,712 B1 | 6/2002 | Rolf | |
| 6,448,462 B2 | 9/2002 | Groitzsch et al. | |
| 6,454,787 B1 | 9/2002 | Maddalo et al. | |
| 6,485,667 B1 | 11/2002 | Tan | |
| 6,486,285 B2 | 11/2002 | Fujita | |
| 6,548,569 B1 | 4/2003 | Williams et al. | |
| 6,552,244 B1 | 4/2003 | Jacques et al. | |
| 6,565,878 B2 | 5/2003 | Schoenfeldt et al. | |
| 6,566,577 B1 | 5/2003 | Addison et al. | |
| 6,599,891 B2 | 7/2003 | North et al. | |
| 6,693,180 B2 | 2/2004 | Lee et al. | |
| 6,726,712 B1 | 4/2004 | Raeder-Devens et al. | |
| 6,863,924 B2 | 3/2005 | Ranganathan et al. | |
| 6,864,245 B2 | 3/2005 | Vournakis et al. | |
| 6,992,233 B2 | 1/2006 | Drake et al. | |
| 7,019,191 B2 | 3/2006 | Looney et al. | |
| 7,371,403 B2 | 5/2008 | McCarthy et al. | |
| 7,402,172 B2 | 7/2008 | Chin et al. | |
| 7,546,812 B2 | 6/2009 | Eastin et al. | |
| 7,637,934 B2 | 12/2009 | Mangiardi et al. | |
| 7,671,102 B2 | 3/2010 | Gaserod et al. | |
| 7,820,872 B2 | 10/2010 | Gregory et al. | |
| 7,850,709 B2 | 12/2010 | Cummins et al. | |
| 7,897,832 B2 | 3/2011 | McAdams et al. | |
| 8,063,265 B2 | 11/2011 | Beck et al. | |
| 2001/0045177 A1 | 11/2001 | Harvey et al. | |
| 2002/0071855 A1 | 6/2002 | Sadozai et al. | |
| 2002/0161376 A1 | 10/2002 | Barry et al. | |
| 2003/0078532 A1* | 4/2003 | Ruszczak et al. | 602/46 |
| 2005/0036955 A1 | 2/2005 | DeGould | |
| 2005/0038369 A1 | 2/2005 | Gregory et al. | |
| 2005/0123581 A1 | 6/2005 | Ringeisen et al. | |
| 2005/0137512 A1 | 6/2005 | Campbell et al. | |
| 2005/0147656 A1 | 7/2005 | McCarthy et al. | |
| 2005/0240137 A1 | 10/2005 | Zhu et al. | |
| 2006/0004314 A1 | 1/2006 | McCarthy et al. | |
| 2006/0008419 A1 | 1/2006 | Hissink et al. | |
| 2006/0083710 A1 | 4/2006 | Joerger et al. | |
| 2006/0184224 A1 | 8/2006 | Angel | |
| 2006/0211973 A1 | 9/2006 | Gregory et al. | |
| 2007/0021703 A1 | 1/2007 | McCarthy et al. | |
| 2007/0066920 A1 | 3/2007 | Hopman et al. | |
| 2007/0083137 A1 | 4/2007 | Hopman et al. | |
| 2007/0237811 A1 | 10/2007 | Scherr | |
| 2007/0255194 A1 | 11/2007 | Gudnason et al. | |
| 2007/0255243 A1 | 11/2007 | Kaun et al. | |
| 2007/0276308 A1 | 11/2007 | Huey et al. | |
| 2008/0132990 A1 | 6/2008 | Richardson | |
| 2008/0147019 A1 | 6/2008 | Song et al. | |
| 2008/0241229 A1 | 10/2008 | Li et al. | |

FOREIGN PATENT DOCUMENTS

| | | |
|---|---|---|
| EP | 0643963 | 3/1995 |
| EP | 1462123 | 9/2004 |
| JP | 60-142927 | 7/1985 |
| JP | 62-039506 | 2/1987 |
| JP | 63-090507 | 4/1988 |
| JP | 07-116241 | 5/1995 |
| JP | 11-342153 | 12/1999 |
| JP | 2002-233542 | 8/2002 |
| WO | WO 95/05794 | 3/1995 |
| WO | WO 99/02587 | 1/1999 |
| WO | WO 00/56256 | 9/2000 |
| WO | WO 02/102276 | 12/2002 |
| WO | WO 02102276 A2 * | 12/2002 |
| WO | WO 03/047643 | 6/2003 |
| WO | WO 03/079946 | 10/2003 |
| WO | WO 03/092756 | 11/2003 |
| WO | WO 03/101310 | 12/2003 |
| WO | WO 2004/047695 | 6/2004 |
| WO | WO 2004/060412 | 7/2004 |
| WO | WO 2005062880 | 7/2005 |
| WO | WO 2006049463 | 5/2006 |
| WO | WO 2006071649 | 7/2006 |
| WO | WO 2007009050 | 1/2007 |
| WO | WO 2007056066 | 5/2007 |
| WO | WO 2007074327 | 7/2007 |
| WO | WO 2008033462 | 3/2008 |
| WO | WO 2008036225 | 3/2008 |

OTHER PUBLICATIONS

Wu et al., "Development of In Vitro Adhesion Test for Chitosan Bandages," Society for Biomaterials 30th Annual Meeting Transactions (2005).*

USPTO Office Action dated Apr. 13, 2009, regarding U.S. Appl. No. 11/485,886, 43 pages.

Sanford et al. "Chitin an dChitosan, Sourcces, Chemistry, Biochemistry, Physical Porperties and Applications", Proceedings from the 4th International Conference on Chitin and Chitosan held in Trondheim, Norway, Aug. 22-24, 1988, Elsevier Science Publishers Ltd. 1989, pp. 51-69.

Sandford, Biomedical Applications of New Forms of Chitin/Chitosan, *Chitin Derivatives in Life Science*, 1992.

Sondeen et al., "Comparison of 10 Different Hemostatic Dressings in an Aortic Injury" J Trauma. 2003: 54: 280-285.

Pusateri et al., "Advanced Hemostatic Dressing Development Program: Animal Model Selections Criteria and Results of a Study of Nine Hemostatic Dressings in a Model of Severe Large Venous Hemorrhage and Hepatic Injury in Swine" J Trauma. 2003; 55: 512-526.

HemCon Bandage Manufacturing Method (Photos and Text), ca. 2007.

HemCon Bandage Training DVD (Photo), ca 2007.

Wedmore et al., "A Special Report on Chitosan-Based Hemostatic Dressing: Experience in Current Combat IOperations" J Trauma. 2006; 60: 655-658.

(56) References Cited

OTHER PUBLICATIONS

Wislon, "The Army's Greatest Inventions" U.S Army Material Command, 2005 Edition: 30-37.
Portland Business Journal Nov. 4, 2006 "HemCon Bandage Stakes Claim to Soldier's Kit Bag".
Poster Presentation: Horsch et al."Prehospital Use of HemCon Bandage by Paramedics of Mogen David Adom the Israeli National EMS System" May 2007.
Poster Presentation: Belman et al. "From the Battlefield to the Street—Experience of a Suburban Fire/EMS Agency with Chitosan Dressing" Aug. 2006.
Siek, Fortune Small Business, Jul./Aug. 2006: 67-68.
Transcript of CNN Segment Jun. 8, 2006.
Fwu-Long Mi et al., "Fabrication and Characterization of a sponge-like asymmetric chitosan membrane as a wound dressing," Biomaterials 22 pp. 165-173 (2001), Elsevier Science Ltd., London and New Yorko.
Michele W. Chan et al., "Comparison of Poly-N-acetyl Glucosamine (P-GlcNAc) with Absorbalbe Collagen (Actifoam), and Fibrin Sealant (Bolheal) for Achieving Hemostatis in a Swine Model of Splenic Hemorrhage," The Journal of Trauma 489(3) pp. 454-458 (2000) Lippincott Williams & Wilkins, Inc. USA.
David J. Cole et al., "A pilot study evaluating the efficacy of a fully acetylated poly-N-acetyl glucosamine membrane formulation as a topical hemostatic agent," Surgery 126(3) pp. 510-517 (1999) Mosby, Inc. usa.
Paul A. Sanford et al., "Biomedical Applicants of High-Purity Chitosan," ACS Symposium Series 467 pp. 430-445 (1991), American Chemical Society, Washington, D.C.
William G. Malette et al. "Chitosan: A New Hemostatic ," The Annals of Thoracic Surgery 36(1) pp. 55-58 (1983).
Roger Olsen et al., "Biomedical Applicants of Chitin and its Derivatives," Chitin and Chitosan pp. 813-829 (1988), Elsevier Applied Science, London and New York.
Allan et al., "Biomedical Applications of Chitin and Chitosan." Chitin, Chitosan, and Related Enzymes—Accademic Press, Inc.: 119-133, 1984.
Anema et al., "Potential Uses of Absorbable Fibrin Adhesive Bandage for Genitourinary Trauma." World Journal of Surgery, vol. 25: 1573-1577, 2001.
Bégin et al., "Antimicrobial films produced from chitosan." International Journal of Biological Macromolecules, vol. 26: 63-67, 1999.
Kiley, Kevin, "Department of the Army memo." Jul. 20, 2005.
Kumar, Ravi, "Chitin and chitosan fibres: A review." Bulletin of Material Science: vol. 22, No. 5: 905-915, Aug. 1999.
Luo et al., "The role of poly(ethylene glycol) in the formation of silver nanoparticles." Journal of Colloid and Interface Science, vol. 288: 444-448, 2005.
Martin et al., "Medical applications of poly-4-hydroxybutyrate: a strong flexible absorbable biomaterial." Biochemical Engineering Journal, vol. 16: 97-105, 2003.
Ohshima et al., "Clinical Application of Chitin Non-Woven Fabric as Wound Dressing." European Journal of Plastic Surgery, vol. 10: 66-69, 1987.
Ohshima et al., "Clinical application of new chitin non-woven fabric and new chitin sponge sheet as wound dressing." European Journal of Plastic Surgery, vol. 14: 207-211, 1991.
Percot et al., "Optimization of Chitin Extraction from Shrimp Shells." Biomacromolecules, vol. 4: 12-18, 2003.
Park et al., "Platelet derived growth factor releasing chitosan sponge for periodontal bone regeneration." Biomaterials, vol. 21: 153-159, 2000.
Bendix, "Chemical synthesis of polyactide and its copolymers for medical applications." Polymer Degradation and Stability, vol. 59: 129-135, 1998.
Database WPI, Week 200873 Thomson Scientific, London GB, AN 2008-M34232, XP002965596 & CN 101138648, Mar. 12, 2008.

\* cited by examiner

20mm 1.0mm

5mm

WOUND DRESSING AND METHOD FOR CONTROLLING SEVERE, LIFE-THREATENING BLEEDING

RELATED APPLICATIONS

This application is a continuation of application Ser. No. 12/148,320 filed 18 Apr. 2008, which is a divisional of application Ser. No. 10/743,052 filed 23 Dec. 2003, which is a continuation-in-part under 37 C.F.R. §1.53(h) of U.S. patent application Ser. No. 10/480,827, filed on Dec. 15, 2003, for Wound Dressing and Method of Controlling Severe Life-Threatening Bleeding, which was a national stage filing under 37 C.F.R. §371 of International Application No. PCT/U502/18757, filed on Jun. 14, 2002.

FIELD OF THE INVENTION

This invention is directed to hemorrhage control wound dressings, and methods of using and producing such dressings. The subject wound dressing is constructed from a non-mammalian material for the control of severe bleeding. The wound dressing is formed of a biomaterial comprising chitosan and/or other hydrophilic polymers for controlling severe bleeding. The material may alternatively comprise polyacrylic acid or a combination of polyacrylic acid with other polymers. The kind of severe, life-threatening bleeding contemplated by this invention is of the type not capable of being stanched when a conventional gauze wound dressing is applied with conventional pressure to the wound. The wound dressing is capable of substantially stanching the flow of life-threatening bleeding from a wound by adhering to the wound site, sealing the wound, accelerating blood clot formation at the wound site, reinforcing clot formation at the wound site, preventing bleed out from the wound site, and substantially prohibiting the flow of blood out of the wound site.

BACKGROUND OF THE INVENTION

An advanced hemorrhage control bandage and methods of its application would substantially augment available hemostatic methods. To date, the application of continuous pressure with gauze bandage remains the preferred primary intervention technique used to stem blood flow, especially flow from severely bleeding wounds. However, this procedure neither effectively nor safely stanches severe blood flow. This has been, and continues to be, a major survival problem in the case of severe life-threatening bleeding from a wound.

Furthermore, it is widely accepted that severe bleeding is the leading cause of death from wounds on the battlefield, accounting for approximately 50 percent of such deaths. It is estimated that one-third of these deaths could be preventable with enhanced hemorrhage control methods and devices. Such enhanced hemorrhage control would also prove very useful in non-military settings, e.g., hospitals and veterinary clinics, where hemorrhage is the second leading cause of death following trauma.

Currently available hemostatic bandages such as collagen wound dressings or dry fibrin thrombin wound dressings are restricted to use in surgical applications, and are not sufficiently resistant to dissolution in high blood flow. They also do not possess enough adhesive properties to serve any practical purpose in the stanching of severe blood flow. These currently available surgical hemostatic bandages are also delicate and thus prone to failure should they be damaged by bending or loading with pressure. They are also susceptible to dissolution in hemorrhagic bleeding. Such dissolution and collapse of these bandages may be catastrophic, because it can produce a loss of adhesion to the wound and allow bleeding to continue unabated.

There is prior art relating to chitosan and chitosan dressings. For example, U.S. Pat. No. 4,394,373 issued to Malette et al, employs chitosan in liquid or powder form to agglutinate blood in microgram/mL quantities. Also, U.S. Pat. No. 4,452,785 issued to Malette et al. is directed to a method of occluding blood vessels therapeutically by injecting chitosan directly into the vessels. U.S. Pat. No. 4,532,134 issued to Malette et al, further relates to hemostatis, inhibiting fibroplasias, and promoting tissue regeneration by placing in contact with the tissue wound a chitosan solution or water-soluble chitosan. The chitosan forms a coagulum, which prevents bleeding.

U.S. Pat. No. 5,858,350 issued to Vournakis et al, relates to a process to make diatom derived biomedical grade, high purity chitin and chitin derivatives (so called protein-free even though this is not demonstrated by analysis in the patent). The proposed advantage of so called protein-free chitin/chitosan materials are that they should be significantly less antigenic than current shrimp and crab derived chitin materials.

Mi, F L., et al., "Fabrication and Characterization of a Sponge-Like Assymetric Chitosan Membrane as a Wound Dressing", Biomaterials, 22(2): 165-173 (2001) describes the fabrication and wound healing function of an asymmetric chitosan membrane produced by a phase inversion method.

Chan, M W., et al., "Comparison of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage", J. Trauma, Injury, Infection, and Critical Care, 48(3): 454-458 (2000) describes the testing of chitin/chitosan hemostatic patches under the moderate blood flow and oozing typical of the swine spleen capsular stripping test.

Cole, D. J., et al., "A Pilot Study Evaluating the Efficacy of a Fully Acetylated poly-N-acetyl glucosamine Membrane Formulation as a Topical Hemostatic Agent", Surgery 126(3): 510:517 (1999) describes hemostatic agent testing in the swine spleen capsular stripping test.

Sandford, Steinnes A, "Biomedical Applications of High Purity Chitosan" in WATER SOLUBLE POLYMERS, SYNTHESIS, SOLUTION PROPERTIES AND APPLICATIONS, ACS Series 467, (W. S. Shalaby et al. Eds. ACS, Washington, D.C. 1991, Ch 28, 431-445). This is a general review paper describing chitosan use with reference to a chitosan sponge.

Mallette, W. O., et al., "Chitosan: A New Hemostat," Annals of Thoracic Surgery 36(1): 55-58, (1983). See comments concerning the Malette patents above. Olsen, R., et al., In CHITIN AND CHITOSAN, SOURCES, CHEMISTRY, BIOCHEMISTRY, PHYSICAL PROPERTIES AND APPLICATIONS, Elsevier Applied Science, London and New York, 1989, 8 13-828. This paper concerns the agglutinating efficiency of chitosan. Japanese Patent 60142927 covers a chitosan medical band with improved tack. Japanese patent 63090507A2 describes a water insoluble and 2% acetic acid insoluble chitosan sponge for external hemostatic application or for protection of a wound.

U.S. Pat. No. 5,700,476 describes collagen based structurally inhomogeneous sponges for wound dressings and/or implant applications formed by freeze drying techniques employing at least one pharmacological agent and at least one substructure.

U.S. Pat. No. 2,610,625 relates to freeze dried sponge structures that are highly effective in stopping the flow of blood or other fluids and which will be absorbed after a time in the body. This patent describes collagen sponge preparation.

U.S. Pat. No. 5,836,970 comprises a wound dressing formed of a blend or mixture of chitosan and alginate.

Thus, there is a need for improved hemostatic bandages able to stanch of severe blood flow and that will not fail upon bending or loading with pressure.

SUMMARY OF THE INVENTION

The invention is directed to a first-aid/primary intervention wound dressing for control of severe, life-threatening bleeding. Presently there are no low cost wound dressings that are suitable for control of severe life-threatening bleeding. There is a need for this type of dressing especially in the battlefield, where typically 50% of all deaths are associated with an inability to immediately control severe bleeding. The wound dressing of the invention is capable of substantially stanching the flow of life-threatening bleeding from a wound by adhering to the wound site, sealing the wound, accelerating blood clot formation at the wound site, reinforcing clot formation at the wound site, preventing bleed out from the wound site, and substantially prohibiting the flow of blood out of the wound site. In one embodiment, a compressed sponge for hemorrhage control comprising a hydrophilic polymer, wherein the compressed sponge has a compressed sponge density of about 0.6 to 0.15 g/cm$^3$ is provided. The hydrophilic polymer may be an alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may be of amylase, amylopectin and a combination of amylopectin and amylase. Preferably, the hydrophilic polymer is chitosan. Preferably, the chitosan has a weight average molecular weight of at least about 100 kDa. More preferably, the chitosan has a weight average molecular weight of at least about 150 kDa. Most preferably, the chitosan has a weight average molecular weight of at least about 300 kDa.

Preferably, the chitosan has a viscosity at 25° C. in a 1% solution of acetic acid (AA) with spindle LVI at 30 rpm which is about 100 centipoise to about 2000 centipoise. More preferably, the chitosan has viscosity at 25° C. in a 1% solution of acetic acid (AA) with spindle LVI at 30 rpm which is about 125 centipoise to about 1000 centipoise. Most preferably, the chitosan has viscosity at 25° C. in a 1% solution of acetic acid (AA) with spindle LV1 at 30 rpm which is about 150 centipoise to about 500 centipoise.

The compressed sponge may further comprise an active ingredient. The active ingredient may include, but is not limited to, calcium, thrombin, factor VIIa, factor XIII, thromboxane A2, prostaglandin-2a, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibroblast growth factor, keratinocyte growth factor, nerve growth factor, penicillin, ampicillin, methicillin, amoxycillin, clavamox, clavulanic acid, amoxicillin, aztreonam, imipenem, streptomycin, Kanamycin, Tobramycin, gentamicin, vancomycin, clindamycin, erythroniycin, polymyxin, bacitracin, amphotericin, nystatin, rifampicin, tetracycline, doxycycline, chloramphenicol and combinations thereof.

In another embodiment, a compressed composite sponge for hemorrhage control comprising a hydrophilic polymer sponge and a wettable polymer matrix or wettable polymer matrices inside the sponge and/or at the sponge surface is provided. The hydrophilic polymer may include alginate, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may be amylase, amylopectin and a combination of both amylopectin and amylase.

The wettable polymer may include non-woven mats, woven mats, molded polymer mesh and low density sponges. The wettable polymer may include, but is not limited to a chitin, an alginate, a neutralized chitosan, a re-acetylated chitosan, a poly(glycolic acid), a poly(lactic acid), a poly(e-caprolactone), a poly(β-hydroxybutyric acid), a poly(β-hydroxyvaleric acid), a polydioxanone, a poly(ethylene oxide), a poly(malic acid), a poly(tartronic acid), a polyphosphazene, a polyethylene, a polypropylene, a metallocene polymer, a polyurethane, a polyvinylchloride polymer, a polyester, a polyamide and combinations thereof. Preferably, the hydrophilic polymer is chitosan.

Preferably, the chitosan has a weight average molecular weight of at least about 100 kDa. More preferably, the chitosan has a weight average molecular weight of at least about 150 kDa. Most preferably, the chitosan has a weight average molecular weight of at least about 300 kDa. Preferably, the chitosan has viscosity at 25° C. in a 1% solution of acetic acid (AA) which is about 100 centipoise to about 2000 centipoise. More preferably, the chitosan has viscosity at 25° C. in a 1% solution of acetic acid (AA) which is about 125 centipoise to about 1000 centipoise. Most preferably, the chitosan has viscosity at 25° C. in a 1% solution of acetic acid (AA) which is about 150 centipoise to about 500 centipoise.

The sponge may comprise a textile thread impregnated with a hydrophilic polymer. The textile thread is impregnated with a hydrophilic polymer. Preferably, the hydrophilic polymer is chitosan. The hydrophilic polymer may also include, but is not limited to an alginate, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may include amylase, amylopectin and a combination of both amylopectin and amylase.

The wettable mesh may be a non-woven mesh. Preferably, the sponge contains pores with pore diameters of about 15 microns to about 300 microns, More preferably, the sponge contains pores with pore diameters of about 30 microns to about 250 microns. More preferably, the sponge contains pores with pore diameters of about 100 microns to about 225 microns. More preferably, the sponge contains pores with pore diameters of about 125 microns to about 200 microns. Most preferably, the sponge contains pores with pore diameters of about 150 microns to about 175 microns. Preferably, the sponge has an available blood contacting surface area per base surface of the sponge of about 100 cm2 per cm2 to about 1000 cm2 per cm2. More preferably, the compressed composite sponge has an available blood contacting surface area per base surface of the sponge of about 200 cm$^2$ per cm$^2$ to about 800 cm$^2$ per cm$^2$. Most preferably, the sponge has an available blood contacting surface area per base surface of the sponge of about 300 cm$^2$ per cm$^2$ to about 500 cm$^2$ per cm$^2$. Preferably, the available mass of chitosan biomaterial per wound surface area is about 0.02 g/cm$^2$ to about 1.0 g/cm$^2$. More preferably, the available mass of chitosan biomaterial per wound surface area is about 0.04 g/cm$^2$ to about 0.5 g/cm². Most preferably, the available mass of chitosan biomaterial per wound surface area is about 0.06 g/cm² to about 0.1 g/cm².

The compressed composite sponge further may comprise a backing support layer. The backing support layer may be a layer of polymeric material. The polymeric material may be a synthetic non-biodegradable material or a naturally occurring biodegradable polymer. The synthetic biodegradable materials may include poly(glycolic acid), poly(lactic acid), poly(e-caprolactone), poly(β-hydroxybutyric acid), poly-hydroxyvaleric acid), polydioxanone, poly(ethylene oxide), poly (malic acid), poly(tartronic acid), polyphosphazene, copolymers of polyethylene, copolymers of polypropylene, the copolymers of the monomers used to synthesize said polymers or combinations thereof The naturally occurring polymers may include chitin, algin, a starch, dextran, collagen, albumen and a combination thereof. The synthetic polymers may include polyethylene, polypropylene, a metallocene polymer, a polyurethane, a polyvinylchloride polymer, a polyester, a polyamide or combinations thereof.

Preferably, the compressed composite sponge has a degree of adhesion to the wound site of about 40 kPa to about 500 kPa. More preferably, the compressed composite sponge has a degree of adhesion to the wound site of about 60 kPa to about 250 kPa. Most preferably, the compressed composite sponge has a degree of adhesion to the wound site of about 100 kPa to about 200 kPa. The compressed composite sponge is capable of forming an adhesive material in combination with blood flowing from said wound at a wound dressing-blood interface, Preferably, the adhesive material is a chitosan adhesive material.

Preferably, the chitosan adhesive material has a pH of not more than about 6.3 when the wound is sealed. More preferably, the chitosan adhesive material preferably has a pH of not more than about 4.5 when the wound is sealed. Most preferably, the chitosan adhesive material has a pH of not more than about 4.0 when the wound is sealed.

The adhesive material may comprise an acid selected from the group consisting of acetic acid, formic acid, lactic acid, ascorbic acid, hydrochloric acid and citric acid. Preferably, the compressed composite sponge has a thickness that is not less than about 3.0 mm and not more than about 8 mm. More preferably, the compressed composite sponge has a thickness that is not less than about 3.5 mm and not more than about 7 mm. Most preferably, the compressed composite sponge has a thickness that is not less than about 4.0 mm and not more than about 6 mm. Preferably, the compressed composite sponge has an ultimate tensile stress about 0.1 MPa to about 10 MPa. More preferably, the compressed composite sponge has an ultimate tensile stress of about 0.15 MPa to about 0.8 MPa. Most preferably, the compressed composite sponge has an ultimate tensile stress of about 0.25 MPa to about 0.5 MPa. Preferably, the compressed composite sponge has an ultimate elongation of about 5%. More preferably, the compressed composite sponge has an ultimate elongation of about 10%. Most preferably, the compressed composite sponge has an ultimate elongation of about 15%.

In another embodiment, a process for preparing a compressed sponge for hemorrhage control comprising (a) freezing/freeze drying preparation of a low density sponge; and (b) compressing the low density sponge at a preferred rate of about 10 mm per minute and at a preferred controlled temperature of 80° C. thereby obtaining a compressed sponge with a density of about 0.1 to about 0.2 g/cm³, is provided.

In another embodiment a process for preparing a compressed sponge for hemorrhage control comprising (a) preparation of a low density sponge by methods other than freezing/freeze drying preparation of a low density sponge; and (h) compressing the subsequent low density sponge at a rate of about 10 mm per minute and at a preferred controlled temperature of about 80° C. thereby obtaining a compressed sponge with a density of about 0.1 to about 0.2 g/cm³, is provided. Preferably, the low density sponge has a density of about 0.01 g/cm³ to about 0.035 g/cm³. Preferably, the compressed sponge has a density of about 0.1 g/cm³ to about 0.15 g/cm³.

In another embodiment, a process for preparing a compressed composite sponge for hemorrhage control comprising a) degassing chitosan biomaterial solution by heating the chitosan biomaterial solution and applying a vacuum thereto; h) freezing the chitosan biomaterial solution; c) removing water from within frozen chitosan biomaterial without damaging the structural integrity of the frozen chitosan biomaterial so that the water in the chitosan biomaterial passes from a solid phase into a gas phase; d) compressing the chitosan biomaterial at a preferred rate of about 10 mm per minute thereby obtaining a compressed sponge with a density of about 0.1 to about 0.2 g/cm³ and e) baking the compressed chitosan sponge at 80° C. for 30 minutes. Preferably, the temperature is gradually lowered over a predetermined period of time during the freezing of the chitosan biomaterial of step (b).

Preferably, the temperature of step (b) is a final freezing temperature of not more than about –25° C. More preferably, the process of step (b) involves a final freezing temperature of not more than about –35° C. Most preferably, the temperature of step (h) is a final freezing temperature of not more than about –45° C. The water removal may be performed by freeze-drying the frozen chitosan biomaterial. The process may further comprise a step of adding argon, nitrogen and helium hack into the degassed chitosan solution before the freezing.

The compressed sponge may be sterilized. Preferably, the compressed sponge is sterilized by gamma irradiation.

In another embodiment, a method of preventing severe bleeding in a subject comprising administering a compressed sponge or a compressed composite sponge is provided. Preferably, the subject is a mammal. More preferably, the mammal is human. Preferably, the subject is suffering from severe bleeding such that about 30-40% total blood volume loss would result within 20 to 30 minutes if the bleeding was left uncontrolled. Preferably, the compressed sponge or compressed composite sponge is applied with about 60 to 80 kPa pressure directly over the bleeding injury and held in place for 3 to 5 minutes before releasing, packing and wrapping.

In another embodiment, a bandage kit for treating severe bleeding comprising a compressed sponge or a composite compressed sponge, gauze rolls for packing and an Ace bandage for wrapping a wound is provided. In another embodiment, a process for mechanical mating and meshing of the compressed or composite compressed sponges comprising pressing tissue contacting sides of the sponge against a macrotextured surface is provided. The macrotextured surface may include surfaces prepared by chemical etching, surfaces prepared by ion beam surface ablation, surfaces prepared by mechanical cutting and surfaces prepared by laser ablation.

In another embodiment, a process for improving the mechanical traction of the compressed or compressed composite sponges comprising pressing tissue contacting sides of the sponge against a macrotextured surface is provided. Preferably, the macrotextured surface is selected from the group consisting of surfaces prepared by chemical etching, and surfaces prepared by particle blasting techniques.

In another embodiment, a process for limiting or stopping the formation of coarse crust on the surface of the composite or compressed composite sponges comprising covering the surface of the sponge with a polymer film, a polymer plate, an elevated plastic plate or a moisture impermeable, breathable membrane film is provided.

In another embodiment, a low density sponge, wherein the sponge is formed by compressing a sponge with an initial density of about less than 0.05 g/cm³ until the sponge reaches a density of about less than 0.08 g/cm³. The sponge can be formed by a process other than freezing or freeze drying. Preferably, the sponge is formed using a method selected from the group consisting of a phase inversion process, sponges prepared by covalent binding of active components to preformed matrices, and foaming techniques.

In another embodiment, the compressed sponge and compressed composite sponge may farther comprise at least one additional hydrophilic polymer. The additional hydrophilic polymer may include, but is not limited to, alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may include, but is not limited to, amylase, amylopectin and a combination of amylopectin and amylase. Preferably, the hydrophilic polymer is chitosan.

Another embodiment provided for is, a compressed sponge for hemorrhage control comprising a hydrophilic polymer, wherein the compressed sponge has a compressed sponge density of about 0.6 to 0.15 g/cm³ the hydrophobic polymer may be a is polyacrylic acid. Preferably, the compressed sponge may further comprise an active ingredient. The active ingredient may include, but is not limited to, calcium, thrombin, factor Vila, factor XIII, thromboxane A2, prostaglandin-2a, epidermal growth factor, platelet derived growth factor, Von Willebrand factor, tumor necrosis factor (TNF), TNF-alpha, transforming growth factor (TOF), TGF-alpha, TOE-beta, insulin like growth factor, fibroblast growth factor, keratinocyte growth factor, nerve growth factor, penicillin, ampicillin, methicillin, amoxycillin, clavamox, clavulanic acid, amoxicillin, aztreonam, imipenem, streptomycin, Kanamycin, Tobramycin, gentamicin, vancomycin, clindamycin, erythromycin, polymyxin, bacitracin, amphotericin, nystatin, rifampicin, tetracycline, doxycycline, chloramphenicol or combinations thereof.

In another embodiment, a compressed composite sponge for hemorrhage control comprising a hydrophilic polymer sponge and a wettable polymer matrix or wettable polymer matrices inside the sponge and/or at the sponge surface; wherein the hydrophobic polymer is polyacrylic acid is provided. The wettable polymer matrices may include non-woven mats, woven mats, molded polymer mesh and low density sponges. The wettable polymer matrix may include a chitin, an alginate, a neutralized chitosan, a re-acetylated chitosan, a poly(glycolic acid), a poly(lactic acid), a poly(e-caprolactone), a poly(β-hydroxybutyric acid), a poly(β-hydroxyvaleric acid), a polydioxanone, a poly(ethylene oxide), a poly (malic acid), a poly(tartronic acid), a polyphosphazene, a polyethylene, a polypropylene, a metallocene polymer, a polyurethane, a polyvinylchloride polymer, a polyester, a polyamide or combinations thereof.

The sponge may comprise a textile thread impregnated with a hydrophilic polymer. Preferably, the textile thread is impregnated with a hydrophilic polymer, wherein the hydrophobic polymer is polyacrylic acid. Preferably, the wettable polymer matrice is a non-woven mesh.

Preferably, the sponge contains pores with pore diameters of about 15 microns to about 300 microns. More preferably, the sponge contains pores with pore diameters of about 30 microns to about 250 microns. More preferably, the sponge contains pores with pore diameters of about 100 microns to about 225 microns. More preferably, the sponge contains pores with pore diameters of about 125 microns to about 200 microns. Most preferably, the sponge contains pores with pore diameters of about 150 microns to about 175 microns. Preferably, the sponge has an available blood contacting surface area per base surface of the sponge of about 100 cm² per cm² to 1000 cm² per cm². More preferably, the sponge has an available blood contacting surface area per base surface of the sponge of about 200 cm² per cm² to 800 cm² per cm². Most preferably, the sponge has an available blood contacting surface area per base surface of the sponge of about 300 cm² per cm² to about 500 cm² per cm².

The compressed composite sponge may further comprise a backing support layer. Preferably, the backing support layer may be a layer of polymeric material. Preferably, the polymeric material is a synthetic non-biodegradable material or a naturally occurring biodegradable polymer. The synthetic biodegradable materials may include, but is not limited to, poly(glycolic acid), poly(lactic acid), poly(e-caprolactone) poly(β-hydroxybutyric acid), poly(β-hydroxyvaleric acid), polydioxanone, poly(ethylene oxide), poly(malic acid), poly (tartronic acid), polyphosphazene, copolymers of polyethylene, copolymers of polypropylene, the copolymers of the monomers used to synthesize said polymers or combinations thereof The naturally occurring polymers may include, but are not limited to, chitin, algin, a starch, dextran, collagen, albumen, or combinations thereof. The synthetic polymers may include, but are not limited to, polyethylene, polypropylene, a metallocene polymer, a polyurethane, a polyvinylchloride polymer, a polyester, a polyamide or combinations thereof.

Preferably, the compressed composite sponge has a degree of adhesion to the wound site of at about 40 kPa to 500 kPa. More preferably, the compressed composite sponge has a degree of adhesion to the wound site of about 60 kPa to 250 kPa. Most preferably, the compressed composite sponge has a degree of adhesion to the wound site of about 100 kPa to 200 kPa.

The compressed composite sponge may be capable of forming an adhesive material in combination with blood flowing from said wound at a wound dressing-blood interface. Preferably, the adhesive material preferably has a pH of not less than about 5.5 when the wound is sealed. More preferably, the adhesive material preferably has a p11 of not more than about 6.5 when the wound is sealed. Most preferably, the adhesive material preferably has a p11 of not more than about 7.5 when the wound is sealed. Preferably, the adhesive material comprises an acid selected from the group consisting of acetic acid, formic acid, lactic acid, ascorbic acid, hydrochloric acid, and citric acid. Preferably, the compressed composite sponge has a thickness that is not less than about 3.0 mm and not more than about 8 mm. More preferably, the compressed composite sponge has a thickness that is not less than about 3.5 mm and not more than about 7 mm. Most preferably, the compressed composite sponge has a thickness that is not less than about 4.0 mm and not more than about 6 mm. Preferably, the compressed composite sponge has an ultimate tensile stress about 0.1 MPa to about 10 MPa. More preferably, the compressed composite sponge has an ultimate tensile stress of about 0.15 MPa to about 0.8 MPa. Most preferably, the compressed composite sponge has an ultimate tensile stress of about 0.25 MPa to about 0.5 MPa, Preferably, the compressed composite sponge has an ultimate elongation of about 5%. More preferably, the compressed composite sponge has an ultimate elongation of about 10%. Most preferably, the compressed composite sponge has an ultimate elongation of about 15%.

In another embodiment, a process for preparing a compressed sponge for hemorrhage control comprises the steps of (a) freezing/freeze drying preparation of a low density sponge; and (b) compressing the low density sponge at a preferred rate of 10 mm per minute and at a preferred controlled temperature of 80° C. thereby obtaining a compressed sponge with a density of about 0.1 to about 0.2 g/cm³ is provided.

In another embodiment, a process for preparing a compressed sponge for hemorrhage control comprises the steps of (a) preparing a low density sponge by methods other than freezing/freeze drying preparation of a low density sponge; and (b) compressing the subsequent low density sponge at a rate of 10 mm per minute and at a preferred controlled temperature of 80° C. thereby obtaining a compressed sponge with a density of about 0.1 to about 0.2 g/cm3 is provided. Preferably, the low density sponge has a density of about 0.01 g/cm³ to about 0.035 g/cm³. Preferably, the compressed sponge has a density of about 0.1 g/cm³ to about 0.15 g/cm³.

In another embodiment, a process for preparing a compressed composite sponge for hemorrhage control comprises a) degassing biomaterial solution by heating the biomaterial solution and applying a vacuum thereto; b) freezing the biomaterial solution; c) removing water from within frozen biomaterial without damaging the structural integrity of the frozen biomaterial so that the water in the biomaterial passes from a solid phase into a gas phase; d) compressing the biomaterial at a preferred rate of about 10 mm per minute thereby obtaining a compressed sponge with a density of about 0.1 to about 0.2 g/cm³ and e) baking a compressed sponge at 80° C. for 30 minutes is provided. Preferably, the temperature is gradually lowered over a predetermined period of time during the freezing of the biomaterial of step (b). Preferably, the temperature of step (h) is a final freezing temperature of not more than about −5° C. More preferably, the temperature of step (b) is a final freezing temperature of not more than about −35° C. Most preferably, the temperature of step (b) is a final freezing temperature of not more than about −25° C. Preferably, the water removal is performed by freeze-drying the frozen biomaterial. The process may further comprise a step of adding argon, nitrogen and helium back into the degassed chitosan solution before the freezing. The sponge may be compressed sponge is sterilized. Preferably, the compressed sponge is sterilized by gamma irradiation.

In another embodiment, a method of preventing severe bleeding in a subject comprising administering a compressed sponge or a compressed composite sponge is provided. Preferably, the subject is a mammal. More preferably, the mammal is human. Preferably, the subject is suffering from severe bleeding such that about 30-40% total blood volume loss would result within 20 to 30 minutes if the bleeding were left uncontrolled. Preferably, the compressed sponge or compressed composite sponge is applied with about 60 to 80 kPa pressure directly over the bleeding injury and held in place for 3 to 5 minutes before releasing, packing and wrapping the wound.

In another embodiment, a method is provided for preventing severe bleeding in a subject comprises administering a compressed sponge or a compressed composite sponge. Preferably, the subject is a mammal. More preferably, the mammal is human. Preferably, the subject is suffering from severe bleeding such that about 30-40% total blood volume loss would result within 20 to 30 minutes if the bleeding were left uncontrolled. Preferably, the compressed sponge or compressed composite sponge is applied with about 60 to 80 kPa pressure directly over the bleeding injury and held in place for 3 to 5 minutes before releasing, packing and wrapping the wound.

In another embodiment, a bandage kit for treating severe bleeding comprises a compressed sponge or a composite compressed sponge, gauze rolls for packing and an Ace bandage for wrapping a wound is provided.

In another embodiment, a process for mechanical mating and meshing of the compressed or composite compressed sponges comprises pressing tissue contacting sides of the sponge against a macrotextured surface is provided. The macrotextured surface may include surfaces prepared by chemical etching, surfaces prepared by ion beam surface ablation, surfaces prepared by mechanical cutting, and surfaces prepared by laser ablation.

In another embodiment, a process for improving the mechanical traction of the compressed or compressed composite sponges comprises pressing tissue contacting sides of the sponge against a macrotextured surface is provided. Preferably, the macrotextured surface is selected from the group consisting of surfaces prepared by chemical etching, and surfaces prepared by particle blasting techniques.

In another embodiment, a process for limiting or stopping the formation of coarse crust on the surface of the composite or compressed composite sponges comprises covering the surface of the sponge with a polymer film, a polymer plate, an elevated plastic plate or a moisture impermeable, breathable membrane film is provided.

In another embodiment, a low density sponge, wherein the sponge is formed by compressing a sponge with a density of about less than 0.05 g/cm³ until is reaches a density of about less than 0.08 g/cm³, and wherein the sponge is formed by a process other than freezing or freeze drying is provided. Preferably, the sponge is formed using a method selected from the group consisting of a phase inversion process, sponges prepared by covalent binding of active components to preformed matrices and foaming techniques.

In another embodiment, a compressed sponge and compressed composite sponge, wherein the sponges further comprise a hydrophilic polymer in combination with the polyacrylic acid is provided. The hydrophilic polymer may include, but is not limited to, alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may include amylase, amylopectin and a combination of amylopectin and amylase. Preferably, the hydrophilic polymer is chitosan.

DESCRIPTION OF THE DRAWINGS

FIG. 16 shows scanning electron microscopy (SEM) images of the crenulated structure protruding to the top surface of the lamella.

Figure 1:
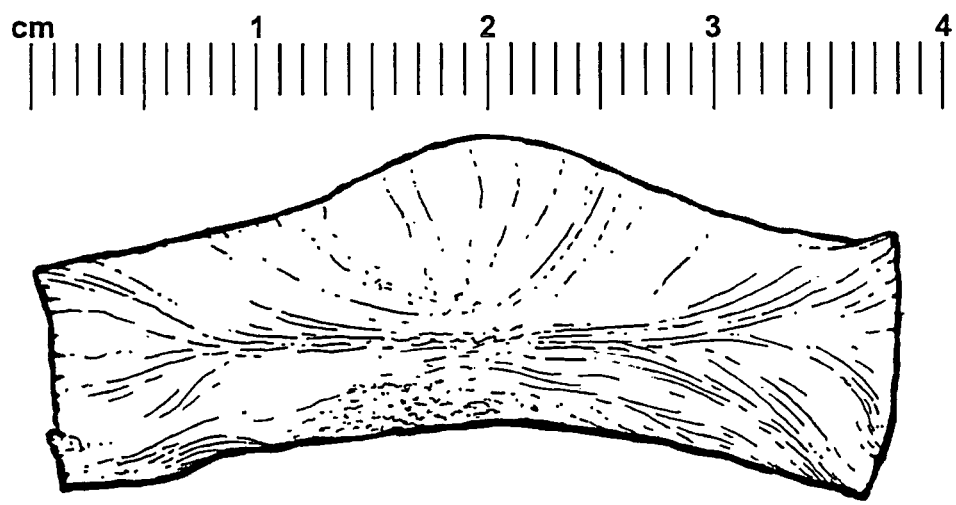
FIG. 1 shows a photo-digital image of transverse cross section through early uncompressed wound dressing.

Fine crenulated structure can be seen protruding normal to the top surface of the lamella.

DETAILED DESCRIPTION OF PREFERRED EMBODIMENTS

A. Compressed Sponges and Compressed Composite Sponges

The invention is directed to a first-aid/primary intervention wound dressing for control of severe, life-threatening bleeding. Such bleeding can be fatal in ballistic injuries and severe arterial lacerations. There is an urgent need for this type of dressing especially in the battlefield, where typically 50% of all deaths are associated with an inability to immediately control severe bleeding.

An advanced wound dressing for control of severe, life-threatening bleeding should preferably have the following properties:
i) easily and quickly applied in one step after removal from package;
ii) rapid and strong blood clotting;
iii) rapid and strong tissue adhesion;
iv) strong internal cohesive properties;
v) rapid and strong wound sealing;
vi) resistant to dissolution under strong blood flow;
vii) good compliance with the injury;
viii) initial good mechanical seating of bandage on tissue to stop slipping by controlled tissue contacting surface-texture; and
ix) ability to be treated roughly without compromising efficacy.

To this end, the invention is directed to advanced hemorrhage control wound dressings, and methods of using and producing such wound dressings. The kind of severe, life-threatening bleeding contemplated by this invention I typically of the type not capable of being stanched when a conventional gauze wound dressing is applied with conventional pressure to the subject wound. Alternatively, the nature of the severe, life-threatening bleeding is such that it is not stanched when a conventional gauze wound dressing is applied with conventional pressure to the wound and, if not controlled by other means, would result in the person lapsing into a state of hypotension. Stated another way, the severe, life-threatening bleeding is generally not capable of being stanched when a conventional gauze wound dressing is applied with conventional pressure to the wound and would result in the systolic blood pressure of the person dropping to a level of less than about 90 mm 1-1 g.

The severe, life-threatening bleeding can also be described as a steady high flow of blood of more than about 90 mL of blood loss per minute, such that in about 20 minutes of bleeding a volume of more than about 40% of total blood from a 70 kg human male would be lost, and the blood volume loss would substantially reduce the likelihood of survival of the person. If this type of bleeding was not stopped within 5-10 minutes, an injured person may lapse into a hypotensive condition, such that arterial blood pressure drops to less than 60 mm Hg. In many cases, the severe bleeding is caused by a ballistic projectile injury or a sharp perforation injury or a blunt traumatic injury. In other cases, the severe bleeding is caused by coagulopathy or internal trauma or surgical trauma, motor vehicle trauma, farming accidents, and the like. The wound dressing of the invention is capable of stanching said severe bleeding which is caused by a substantial arterial wound or a substantial venous wound having a blood flow rate of at least about 90 mL/minute, and adhering to the wound site by the application of direct pressure to the wound dressing for a period of time of not more than about five minutes. The wound dressing also acts quickly to seal the wound, and facilitates substantial clotting and agglutinating of the severe bleeding from the wound site, and stanches the severe bleeding with the temporary application of direct pressure to the wound dressing. The wound dressing has a high resistance to dissolution in high blood flow, and has good internal cohesion properties. It has sufficient flexibility to conform to the injury and toughness to resist rough handling.

The subject dressing is formed of a biomaterial for controlling severe bleeding. Preferably, the biomaterial comprises a non-mammalian material. Preferably, the non-mammalian material is poly [β-(1→34)-2-amino-2-deoxy-D-glucopyranose], more commonly referred to as chitosan.

The wound dressing is formed into a sponge-like or woven configuration via the use of an intermediate structure or form producing steps. The biomaterial comprises an interconnected open porous structure, and/or an oriented open lamella structure, and/or an open tubular structure, and/or an open honeycomb structure, and/or a filamentous structure. The wound dressing has interconnected free-space domains or pores with pore of about 15 microns to about 300 microns; about 30 microns to about 250 microns; about 100 microns to about 225 microns; about 125 microns to about 200 microns; and most preferably about 150 microns to about 175 microns. The wound dressing has an available blood contacting surface area per base surface of said wound dressing of preferably at least about 100 cm2 per cm2, more preferably at least about 200 $cm^2$ per $cm^2$, and most preferably at least about 300 $cm^2$ per $cm^2$. The available mass of chitosan biomaterial per wound surface area is preferably about 0.02 $g/cm^2$ to about 1.0 $g/cm^2$ more preferably, the available mass of chitosan biomaterial per wound surface area is about 0.04 $g/cm^2$ to about 0.5 g/cm² and most preferably, the available mass of chitosan biomaterial per wound surface area is about 0.06 g/cm² to about 0.1 g/cm².

By "per base surface" is meant, for example, that if 1 cm×1 cm of the base surface is taken which is generally contacting the blood, then one would expect blood to see at least 100 cm² of chitosan surface area because of the open sponge structure.

Sponges may be prepared by processes including, but not limited to, phase inversion processes, freezing, freeze drying, covalent binding of active components to preformed matrices and foaming techniques.

Furthermore, the wound dressing has a mean rate of dissolution per base surface area of said wound dressing when adhered to said wound site, at a temperature of about 37° C., of preferably not more than about 0.008 grams per minute per cm², more preferably not more than about 0.005 grams per minute per cm2, and most preferably not more than about 0.002 grams per minute per cm².

The subject wound dressing preferably has a density of at least about 0.05 g/cm³, more preferably at least about 0.07 g/cm³, and most preferably at least about 0.11 g/cm³. It can have a compression loading preferably to a compression density at least about 0.05 g/cm³, more preferably at least about 0.07 g/cm3, most preferably at least about 0.095 g/cm³, and preferably of not more than about 0.2 g/cm³.

The wound dressing of the invention typically contains chitosan with number average molecular weight of at least about 50 kDa, preferably at least about 75 kDa, more preferably at least about 100 kDa, and most preferably at least about 150 kDa (molecular weights determined by Gel Permeation Chromatography relative to polyethylene glycol standards in p1-I 5.5, 0.01 M sodium acetate). Preferably, the chitosan adhesive material has a pH of not more than about 6.3 when the wound is sealed. More preferably, the chitosan adhesive material preferably has a pH of not more than about 4.5 when the wound is sealed. Most preferably, the chitosan adhesive material has a p1-l of not more than about 4.0 when the wound is sealed.

With regard to dressings where the hydrophilic polymer is polyacrylic acid, preferably the adhesive material has a p1-1 of not less than about 5.5 when the wound is sealed. More preferably, the adhesive material preferably has a pH of not less than about 6.5 when the wound is sealed. Most preferably, the chitosan adhesive material has a pH of not less than about 7.5 when the wound is sealed.

The chitosan also preferably has a weight average molecular weight of at least about 100 kDa, more preferably at least about 150 kDa, and most preferably at least about 300 kDa (molecular weights determined by Gel Permeation Chromatography relative to polyethylene glycol standards in pH 5.5, 0.01 M sodium acetate). The chitosan in the wound dressing also has a Brookfield LV DV-II+ viscosity at 25° C. in a 1% solution of acetic acid (AA) with a spindle at about 30 rpm which is preferably about 100 centipoise to about 2000 centipoise, more preferably about 125 centipoise to about 1000 centipoise, and most preferably about 150 centipoise to 500 centipoise. The spindle is preferably spindle LVI, LV2, LV3 or LV4. The molecular weights and viscosities referred to above are in respect to substantially pure chitosan wound dressings and wound dressings formed with an adsorbed surface layer of chitosan. In the case of a wound dressing containing a covalently bound surface layer of chitosan, then lower viscosities and molecular weights of chitosan may be preferred.

The wound dressing of the present invention can comprise cationic chitosan salts for promoting tissue adhesion and tissue sealing. Preferably, the cationic chitosan salts may include, but are not limited to, chitosan formate, chitosan acetate, chitosan lactate, chitosan chloride, chitosan ascorbate and chitosan citrate. The chitosan has a degree of deacetylation, which is typically at least about 70%, preferably at least about 75%, more preferably at least about 80%, most preferably at least about 85%. It is preferable to compact a low density sponge (density <0.03 g/cm³ solid), rather than to compact a medium density sponge (0.1 g/cm³> density >0.5 g/cm³ by volume solid) or a medium density sponge, already at the preferred density, to its optimal density of close to 0.15 g/cm². This is because the process of sponge formation in low density sponge results in significantly thinner wall thicknesses between sponge pores compared to wall thicknesses in medium and higher density sponges. Also these higher density sponges often have a more interconnected structure which increases sponge stiffness and decreases resistance to cracking. The multiple thin walls in the low density sponges, when compressed to higher densities allow for more flexible and tougher sponges than medium and higher density sponges which are produced with more interconnected structure as well as thicker and hence stiffer cell walls.

Sponge densification may be accomplished ether by unidirectional or hi-directional application of a controlled compression rate at a fixed temperature. A preferred sponge densification is accomplished by unidirectional compression at 80° C. and with sponge moisture content between about 2% and 5% w/w. As an example of uni-axial compression, a 10.0 cm (x direction), ×10.0 cm (y direction)×1.70 cm (z direction) was compressed at 10 mm/min in the z direction between flat, horizontally oriented (xy plain), 63.5 cm×50.8 cm aluminum platens in a Geo Knight 394-TS shuttle press at 40 psi. Compression rate was controlled by pressure setting and use of a Parker SPF200B needle valve.

The final sponge thickness of 0.55 cm was controlled by use of at least two spacer bars 50 cm×2 cm×0.55 cm. The initial density of the sponge was 0.033 g/cm³. The density of the sponge after pressing was 0.10 g/cm³. Other spacer controls such as 0.15 cm, 0.35 cm and 0.45 cm height have been used to achieve sponges of 0.375 g/cm³, 0.16 g/cm3 and 0.125 g/cm³ respectively. Bidirectional compression (platen compression in z and x or y directions) can be carried out to reduce a 5 cm×5×1.7 cm sponge to a 2.5 cm×2.5 cm×0.55 cm sponge. Complex shapes may be compressed using vacuum bagging techniques where a closed plastic film is wrapped over the surface of the sponge and air removed from inside the sponge and plastic film jacket to a controlled level by application of a vacuum. A heated roller press may also be used to compress sponge ribbon and other sponge profiles. It is preferred that such sponge ribbons and profiles are reinforced with an internal composite mesh if they are pressed using a roller press. A preferred embodiment of the compression of continuous composite sponge filaments is that the filament is drawn through a heated Teflon™ coated rod die (80° C.), with a controlled taper at the entrance from close to 2.5 mm diameter to 0.67 mm diameter at lull compression.

Conditions of controlled moisture, heat application and compression rate are chosen to optimize ductile compaction while minimizing brittle collapse of the sponge. Brittle collapse of the sponge results in loss of sponge mechanical integrity by cracking. Optimal sponge compaction to fine interconnected zones is best accomplished in sponges with uniform interconnected sphere-like pores (e.g. dodecahedral). The uncompressed sponge pore size is optimal between 30 and 120 microns with polymer wall thickness from 1 to 20 microns. In the case of sponges with lamella or honeycomb-like structure, it is best that the structure is uniformly oriented near 30 to 40 degrees from the normal direction of uniaxial compression. It is possible to obtain such uniform structure during freezing by application of a sheer stress normal to the direction of the thermal gradient. Such sheers are accomplished by application of uniform loading in the direction of the freezing and with reduced loading in the normal direction to the heat loss.

Near vertical structures are less readily compressed without brittle fracture and random channel formation. In fact, course vertical structures that originate from top surface ice nucleation, during freezing in an open mold, lead to a vertical crust layer in the sponge that does not readily compress, causes stiffness in the sponge and rapidly dissolves when contacting blood or aqueous solutions. Also horizontal structures are undesirable since they compress elastically in the bulk and with loss of pore interconnectivity at the surfaces. Also in the lamella-type or honeycomb-like sponges, it is desired that the wall structure have a crenulated or ciliated surface. Such surfaces on lamella or honeycomb walls are achieved under specific conditions during the freezing controlled phase separation of ice and hydrophilic polymer. Usually the crenulations or cilia are orthogonal to the lamella or honeycomb surface protruding from the surface as thin walls, "teeth", "combs" or columns 3 to 10 microns and 3-10 microns in length in the case of crenulations or 2-3 microns in diameter in the case of cilia. They are distributed on the lamella or honeycomb wall, often with maze-like regularity: one wall adjacent another at 5-10 microns separations but always apart. The extent of the crenulations appears to be controlled by the molecular weight of the polymer, its molecular weight distribution, the extent of elongated rod-like solution properties prior to and during phase separation and the cooling regime. On densification, these crenulations act to maintain pore connections by buttressing a desired controlled spacing of lamella to at least about S to 10 microns as lamella are compressed against each other.

Surface cilia and crenulations also play an important role in adhesion by assisting in mechanical anchoring and mating of surfaces. Hence the surface texture of crenulated/ciliated structures is best preserved during densification. This can be achieved by compression of the positive sponge surface into a negative base surface. Ideally the texture of this base surface is the release negative of the crenulated/ciliated surface. Thus, with minimum application of load, the first surface would exactly key into the second surface providing for maximum surface area contact between the two surfaces. Also on removing the first surface from the second, there necessarily would be good release of surfaces without significant surface damage or loss. As well as this micro-keying of surfaces during pressing, it is also possible to create macro-patterning in the sponge surface by application of a designated template surface against which the sponge is pressed during the compression step. Such patterning may include non-slip patterns that would assist with primary hemostatic bandage application to a tissue injury.

Rectangular, cylindrical, spherical, complex forms and composite forms may be compressed to optimal densities for control of hemorrhaging. Sponges can be prepared with composite forms. A typical rectangular composite form could include an insoluble, but wet-able, non-woven or woven mesh within the sponge. This would typically be done by carrying out the sponge forming phase separation process with the mesh present within the pre-sponge solution. A non-woven mesh material is preferred since this material is more compatible with the sponge compression process and is less likely to cause tearing in the sponge during densification. Another embodiment is where a low density chitosan sponge from a 0.25% to 1% chitosan solution has been formed by freeze/freeze drying into a chitosan sponge. This sponge is then re-acetylated to a chitin sponge form by soaking for at least 24 hours in 99% acetic anhydride at room temperature. This re-acetylated sponge can then be applied on or in a chitosan mold solution (1% to 2%), the chitosan solution formed into a sponge by freeze/freeze drying. The composite chitosan sponge reinforced by the chitin sponge is then subsequently pressed to an optimal density. Another embodiment of the composite form is one where a chitosan sponge has been formed, most preferably by a freeze/freeze drying procedure. This chitosan sponge is then neutralized by washing in a 0.1 M NaOH solution, and then rinsed in water to remove residual sodium salts and sodium hydroxide. The neutralized chitosan sponge (now water and blood insoluble) is now placed on or within an aqueous solution of hydrophilic polymer salt solution (pH=7) in a suitable mold. The mold is placed in a freeze/freeze dryer to produce a hydrophilic sponge reinforced with neutralized chitosan sponge. The subsequent composite sponge is then pressed to an appropriate thickness.

A highly preferred cylindrical sponge composite form is that where the sponge is formed within a wetted yarn or textile. The diameter of the sponge and yarn would typically be 1-2 mm. Compression of this yarn, normal to its axis, results in a flexible chitosan impregnated yarn of 0.2 to 0.5 mm in diameter that can be woven into a strong compliant medical bandage tape for administering to internal bleeding injuries and injuries requiring overlaying, and manipulation of multiple lacerated locations to control the bleeding. Such a tape would be extremely convenient for layering to wounds of various degrees of severity including those that are hemorrhagic. The impregnated polymer in the tape would accelerate local clotting as well as adhere firmly to tissue. A chitosan impregnated yarn of this type would provide for accelerated clotting in individuals with compromised normal platelet clotting such as hemophiliacs and persons in shock.

The sponges of the invention may be matted and meshed using mechanical means. Specifically, the side of the sponge that will be contacting the subjects wound and tissue upon use may be pressed against a microtexured surface. The microtexured surface may include, but is not limited to surfaces prepared by mechanical cutting and surfaces prepared by laser ablation. The mechanical traction of the sponge may also be improved by pressing the surface of the sponge that will be in contact with the subjects wound and tissue upon use against a macrotextured surface. The macrotextured surface may include, but is not limited to surfaces prepared by chemical etching, and surfaces prepared by particle blasting techniques.

The sponge may comprise a textile thread impregnated with a hydrophilic polymer. The thread may be any material, synthetic or natural, which may absorb the hydrophilic polymer. For example, the thread may be a vegetable based material. Preferably, the thread is multi-filimented.

The sponge wound dressing may have a hacking support layer attached to it that provides for and that facilitates improved handling and mechanical properties. This backing layer can be attached or bonded to the dressing by direct adhesion with the top layer of chitosan, or an adhesive such as 3M 9942 acrylate skin adhesive, or fibrin glue or cyanoacrylate glue can be employed. This hacking support layer is also preferably substantially blood insoluble. The backing support layer is also preferably substantially blood impermeable. The backing support layer is also preferably substantially biodegradable. The hacking support layer is preferably a material, which allows for firm handling of the bandage during application and non-sticking to hands once bandage has been applied.

Preferably, the material, which forms the backing support is a layer of polymeric material. Examples of preferred backing materials include low-modulus meshes and/or films and/or weaves of synthetic and naturally occurring polymers. Synthetic biodegradable materials may include, but are not limited to, poly(glycolic acid), poly(lactic acid), poly(e-caprolactone), poly(β-hydroxybutyric acid), poly(β-hydroxyvaleric acid), polydioxanone, poly(ethylene oxide), poly (malic acid), poly(tartronic acid), polyphosphazene, copolymers of polyethylene, copolymers of polypropylene, and the copolymers of the monomers used to synthesize the above-mentioned polymers or combinations thereof. Naturally occurring biodegradable polymers may include, but are not limited to, chitin, algin, starch, dextran, collagen and albumen. Non-biodegradable polymers for temporary external wound applications include polyethylene, polypropylene, metallocene polymers, polyurethanes, polyvinylchloride polymers, polyesters, polyamides or combinations thereof.

The wound dressing of this invention has the degree of adhesion to the wound site which is preferably at least about 40 kPa, more preferably at least about 60 kPa, and most preferably at least about 100 kPa. Also, the wound dressing has a thickness that is preferably not less than about 3.0 mm, more preferably not less than about 3.5 mm, and most preferably not less than about 4.0 mm, and preferably not more than about 8.0 mm, more preferably not more than about 7.0 mm, and most preferably not more than about 6.5 mm.

The wound dressing (2.5 cm wide) of this invention preferably has an ultimate tensile breaking load of not less than 1 kg, more preferably at least 1.5 kg and most preferably at least 2.25 kg. This same dressing preferably has an ultimate elongation of at least 5%, more preferably at least 10% and most preferably at least 15%. The Young's modulus of this dressing is preferably less than 10 MPa, more preferably less than 3 MPa and most preferably less than 1 MPa.

The wound dressing preferably includes a supplemental traction surface which is particularly useful for the application of the wound dressing to a wound site which includes a significant amount of surface blood. The supplemental traction surface can comprise at least one outer surface that grips the wound site to avoid slipping of wound dressing, typically in a direction away from the wound site, during use. The supplemental traction surface is preferably in the form of a tread design.

The subject wound dressing is capable of forming an adhesive material in combination with blood flowing from said wound at the wound dressing-blood interface. In this case, the chitosan adhesive material preferably has a pH of not more than about 5.5, more preferably not more than about 4.5, most preferably not more than about 4, when the wound is sealed. Typical acids employed for purposes of adjusting the pH of the chitosan wound dressing are as follows: acetic acid, formic acid, lactic acid, ascorbic acid, hydrochloric acid and citric acid. The mole ratio of acid anion to glucosamine functional groups in the chitosan cation/anion pair to adjust the pH to the level described above is preferably about 0.90, more preferably about 0.75, and most preferably about 0.60.

The wound dressing is capable of being conformed to the configuration of the wound, for engagingly contacting the wound, and for facilitating stanching of the flow of the severe life-threatening bleeding. More particularly, the wound dressing is introduced into the interstices of the wound. More preferably, the wound dressing is capable of being conformed into a tubular configuration. Then, the reconfigured wound dressing is inserted into the wound.

This invention also contemplates a method for controlling severe, life-threatening bleeding from a wound at a wound site of a person. The method comprises providing a wound dressing formed of a biomaterial comprising chitosan, adhering said wound dressing to the wound site and substantially stanching the flow of said severe life-threatening bleeding from said wound. Preferably, the wound is sealed and bleed out is prevented from said wound site. Also, bleeding and the flow of other fluids into and/or out of the said wound site are preferably prevented. The dressing of the invention acts to rapidly produce a strong clot at the bleeding site by agglutinating red blood cells. It can also promote clotting by accelerating the normal platelet clotting pathway. In certain applications, the dissolution rate of the subject wound dressing has been relatively slow compared to the agglutination rate, and this balance produces good results, as agglutination at high rate stops dissolution. This demonstrates the importance of uniformity of the internal and surface structure of the wound dressing. If a substantial defect is present in the wound dressing, such as a channel caused by grain boundaries or minor cracking, then significant blood flow will channel its way along the defect and produce a highly undesirable bleed-through condition, which can flush away the smaller less-viscous agglutination areas as they form. Also significant blood flow at pressure over the wafer surface appears to adversely affect wound adhesion of prior art wound dressing, but not the wound adhesion of the wound dressing of this invention.

An important preferred attribute of the wound dressing of the invention is the means of combining the chitosan with the blood, while achieving mechanical integrity of the resultant "clot" and binding of the clot to the surface immediately adjacent to the injury. The subject wound dressing accelerates blood clot formation at the wound site, reinforces clot formation at the wound site and prevents bleed out from the wound site. It also substantially prevents the flow of blood and other fluids into and/or out of the wound site.

The wound dressing of the present invention maintains its dual capability for clotting and adhesion to a wound site, while also exhibiting a high level of resilience in an extreme environment. The outstanding resilience of this wound dressing is exemplified by the formidable physical properties of the dressing. The subject wound dressing, unlike prior art products described previously, also has an outstanding ability to conform to wound shape while maintaining structural resilience. This structural resilience allows the wound dressing to assume a preferred shape after deformation, without any substantial loss of mechanical properties.

Preferably, the hemorrhage control dressing of the invention includes a surface that grips the wound area to substantially avoid slipping of the dressing during use. Typically, this non-slip surface of the dressing comprises a traction surface. The subject hemorrhage control dressing may benefit from having an effective non-slip surface, such as a traction surface. The subject hemorrhage control dressing can have a smooth and rough side. The rougher side is preferably the tissue or bleeding surface side, if that side also demonstrated better adhesive properties.

A traction surface may improve a dressing ability to control rapid arterial bleeding by providing increased stability of surface contact (better traction) on a well lubricated surface (such as those surfaces which present in the case of severe bleeding). Such a traction surface helps to channel blood, without adversely affecting adhesion kinetics while allowing for a more controlled and stable tissue contact during the critical period of dressing application. For example, the tissue side of the bandage may have a traction surface in the form of a tread design. This tread could prevent the dressing from undergoing traction loss in a direction away from the wound when undergoing application to the wound.

The non-slip surface of the hemorrhage control dressing may be produced with ridges that are non-connecting or blinded to one another, Thus, in turn, the channels formed between the ridges would be fully or partially blinded to one another and thus provide a controlled connection that would provide for a controlled blood flow back into or out of the wound area. The controlled blood flow in the area of dressing application may be maintained by—the ridges or specific types of responsive gates in the hemorrhage control dressing. Ridges on the bottom of a mold for producing the hemorrhage control dressing may include depressions of the type which will permit a non-slip surface, for example, in the form of traction controls such as ridges or the like, in the subject dressings.

Thus, a hemorrhage control dressing may be produced having at least one non-slip surface, such as a traction surface. Also, a method of producing such a dressing could be provided. Finally, a mold to a produce a hemorrhage control dressing may be fabricated.

To treat severe hemorrhage in cases where adhesive base and top surfaces are advantageous, it is possible to design the support backing so that it may be readily peeled away when adhesion and clotting are required on both surfaces.

There are numerous hemorrhage control configurations of the dressing to address a wide range of possible types of hemorrhagic wound. It may be necessary to carry several bandages of differing configurations (for example, in a battlefield situation) so that the injured persons may be treated by the first responder or even potentially by injured persons themselves. The dressing of the invention can tolerate a great deal of physical abuse and still remain an active hemorrhage control platform.

The dressing is ideal for treating focal vascular bleeding as well as small topical wounds. It is also well suited to packing into complex entry wounds where the bleeding site cannot be easily compressed.

Once hemorrhage control is achieved with the current invention, stabilizing an extremity wound, approximating wound edges and creating a durable dressing that will prevent contamination and allow evacuation of the injured for definitive repair are the main requirements for a civilian and a battlefield hemorrhage control dressing. One envisioned configuration of the hemorrhage control dressing is a 10"×18" dressing with a flexible, elastic hacking that can be tightly attached around an extremity and secured with a locking tab such as a permanent adhesive glue via a peel hack surface to itself. This configuration would approximate wound surfaces and add a hemorrhage control surface without compromising blood flow to the distal extremity, and may be applied by a first responder or in some instances by the injured soldier and would be stable under ambulation or extremity movement during transport. It is envisioned that the bandage would be removed by cutting it apart with no adverse adhesion to the wound or skin.

B. Methods of Making Compressed Sponges and Compressed Composite Sponges

A method is provided for producing a wound dressing capable of controlling severe, life-threatening bleeding from a wound at a wound site of a person. Such a method comprises the steps of providing a chitosan biomaterial as described above.

The structure or form producing steps are typically carried out from solution and can be accomplished employing techniques such as freezing (to cause phase separation), non-solvent die extrusion (to produce a filament), electro-spinning (to produce a filament), phase inversion and precipitation with a non-solvent (as is typically used to produce dialysis and filter membranes) or solution coating onto a preformed sponge-like or woven product. In the case of freezing, where two or more distinct phases are formed by freezing (typically water freezing into ice with differentiation of the chitosan biomaterial into a separate solid phase), another step is required to remove the frozen solvent (typically ice), and hence produce the wound dressing without disturbing the frozen structure. This may be accomplished by a freeze-drying and/or a freeze substitution step. The filament can be formed into a non-woven sponge-like mesh by non-woven spinning processes. Alternately, the filament may be produced into a felted weave by conventional spinning and weaving processes. Other processes that may be used to make the said biomaterial sponge-like product include dissolution of added porogens from a solid chitosan matrix or boring of material from said matrix.

Preferably, the chitosan biomaterial is degassed of general atmospheric gases. Typically, degassing is removing sufficient residual gas from the chitosan biomaterial so that, on undergoing a subsequent freezing operation, the gas does not escape and form unwanted large voids or large trapped gas bubbles in the subject wound dressing product. The degassing step may be performed by heating a chitosan biomaterial, typically in the form of a solution, and then applying a vacuum thereto. For example, degassing can be performed by heating a chitosan solution to about 60° C. immediately prior to applying vacuum at about 500 mTorr for about 5 minutes while agitating the solution.

One embodiment of the hydrophilic polymer biomaterial sponge solution treatment is to add certain gases back into the solution after initial degassing. Such gases would include but are not limited to argon, nitrogen and helium. An advantage of this step is that solutions containing partial pressures of these gases form micro-voids on freezing. The microvoid is then carried through the sponge as the ice-front advances. This leaves a well defined and controlled channel that aids sponge pore interconnectivity.

Next, the chitosan biomaterial, which is typically in solution form, is subjected to a freezing step. Freezing is preferably carried out by cooling the chitosan biomaterial solution and lowering the solution temperature from room temperature to a final temperature below the freezing point. In this way, the preferred structure of the wound-dressing product may be prepared. The final freezing temperature is preferably not more than about −10° C., more preferably not more than about −20° C., and most preferably not more than about −30° C. Preferably, the temperature is gradually lowered over a predetermined time period. For example, the freezing temperature of a chitosan biomaterial solution can be lowered from room temperature to −45° C. by application of a constant temperature cooling ramp of between about −0.4° C./min to about −0.8° C./min for a period of about 90 minutes to about 160 minutes.

The frozen chitosan biomaterial may then undergo water removal from within the interstices of the frozen material. This water removal step may be achieved without damaging the structural integrity of the frozen chitosan biomaterial. This may be achieved without producing a substantial liquid phase, which can disrupt the structural arrangement of the ultimate wound dressing. Thus, the chitosan biomaterial passes from a solid frozen phase into a gas phase without the substantial formation of an intermediate liquid phase.

The preferred manner of implementing water removal is by employing a freeze-drying step. Freeze-drying of the frozen chitosan biomaterial can be conducted by further freezing the frozen chitosan biomaterial. Typically, a vacuum is then applied. Next, the evacuated frozen chitosan material may be heated. Then, there the heated, evacuated, frozen chitosan material is preferably dried.

More specifically, the frozen chitosan biomaterial may be subjected to subsequent freezing preferably at about −15° C., more preferably at about −25° C., and most preferably at about −45° C., for a preferred time period of at least about 1 hour, more preferably at least about 2 hour, and most preferably at least about 3 hour. This step can be followed by cooling of the condenser to a temperature of less than about −45° C., more preferably at about −60° C., and most preferably at about −85° C. Next, a vacuum in the amount of preferably at most about 150 mTorr, more preferably at most about 100 mTorr, and most preferably at least about 50 mTorr, can be applied. Then, the evacuated frozen chitosan material can be heated preferably at about −25° C., more preferably at about −15° C., and most preferably at about −10° C., for a preferred time period of at least about 1 hour, more preferably at least about 5 hour, and most preferably at least about 10 hour. Finally, drying can be conducted at preferably at a temperature of about 20° C., more preferably at about 15° C., and most preferably at about 10° C., for a preferred time period of at least about 36 hour, more preferably at least about 42 hour, and most preferably at least about 48 hour.

Subsequently, the chitosan biomaterial may be compressed, for example by using heated platens to reduce the thickness and increase the density of said wound dressing. The compression temperature is preferably not less than about 60° C., more preferably it is not less than about 75° C. and not more than about 85° C. Then, the pressed chitosan biomaterial is preferably preconditioned by heating same to a temperature of preferably up to about 75° C., more preferably to a temperature of up to about 80° C., and most preferably to a temperature of preferably up to about 85° C. Preconditioning is typically conducted for a period of time up to about 0.25 hours, preferably up to about 0.35 hours, more preferably up to about 0.45 hours, and most preferably up to about 0.50 hours, thereby increasing the adhesion strength and dissolution resistance of said wound dressing, as previously described above.

The processed wound dressing may then be subjected to a sterilization step. The dressing can be sterilized by a number of methods. For example, a preferred method is by irradiation, such as by gamma irradiation, which can further enhance the blood dissolution resistance, the tensile properties and the adhesion properties of the wound dressing. The irradiation can be conducted at a level of at least about 5 kGy, more preferably a least about 10 kGy, and most preferably at least about 15 kGy. The sterilized wound dressing can be subsequently packaged for storage in a heat sealed pouch purged with an inert gas such as either argon or nitrogen gas.

A wound dressing is produced from the chitosan biomaterial, which is capable of substantially stanching the flow of severe life-threatening bleeding from a wound by adhering the wound dressing to the wound site. The wound dressing is preferably sealed to said wound and prevents bleed out from said wound site by adhering said wound dressing to said wound site employing clotting and agglutinating of the severe bleeding. This wound dressing preferably adheres strongly to the wound site, while clotting and agglutinating red blood cells from around the wound, so that pressure need only be employed preferably in the first five minutes of application. In one form of this invention, the device is designed to be a temporary dressing that is applied, even by unskilled practitioners, in order to keep the wounded person alive until expert medical intervention is possible.

C. Active Agents used in Compressed Sponges

The compressed sponge may further comprise an active ingredient. The active ingredient may be, but is not limited to, human serum albumen, calcium, bovine thrombin, human Thrombin (hThrombin), rhThromhin, factor VIIa, factor XIII, recombinant Factor XIII (rFactor XIII), thromhoxane A2, prostaglandin-2a, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibroblast growth factor, keratinocyte growth factor, nerve growth factor, penicillin, ampicillin, methicillin, amoxycillin, clavamox, clavulanic acid, amoxicillin, aztreonam, imipenem, streptomycin, Kanamycin, Tobramycin, gentamicin, vancomycin, clindamycin, erythromycin, polymyxin, bacitracin, amphotericin, nystatin, rifampicin, tetracycline, doxycycline and chloramphenicol, or combinations thereof depending on the nature of the wound or the medical condition of the patient. For example, wounds received in a military setting may comprise an antibiotic, an antifungal, and a clotting factor. Cancer patients in surgery may receive a different combination of active agents.

Example 1

Hemorrhage Control Testing

Table 1 provides a list of the main chitosan materials acquired for hemorrhage control testing. With the exception of the Gelfoam™+thrombin, and Surgicel™ controls for swine spleen experiments and the Johnson and Johnson 4"×4" gauze control for use in swine aortic perforations, the dressing materials described here were all chitosan-based.

Aqueous solutions (2.00% w/w) were prepared in clean, sterile, 1 liter Pyrex flasks from Ametek, ultrafiltered (UF) water and dry chitosan. In the case of the Carbomer, Primex and Genis chitosan materials, 1.0% or 2.0% w/w of glacial acetic acid (Aldrich 99.99%) was added to the aqueous mixtures. Dissolution was achieved by shaking of the flask at 40° C. for 12 to 48 hours. The solutions were degassed by application of vacuum at 500 mTorr at room temperature immediately prior to freezing.

Figure 2:
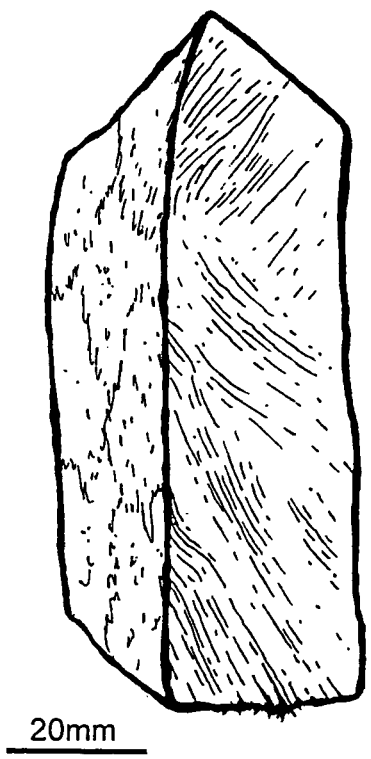
FIG. 2 shows a photo-digital image of transverse cross section through oriented lamella structures in uncompressed wound dressing.
Figure 3:
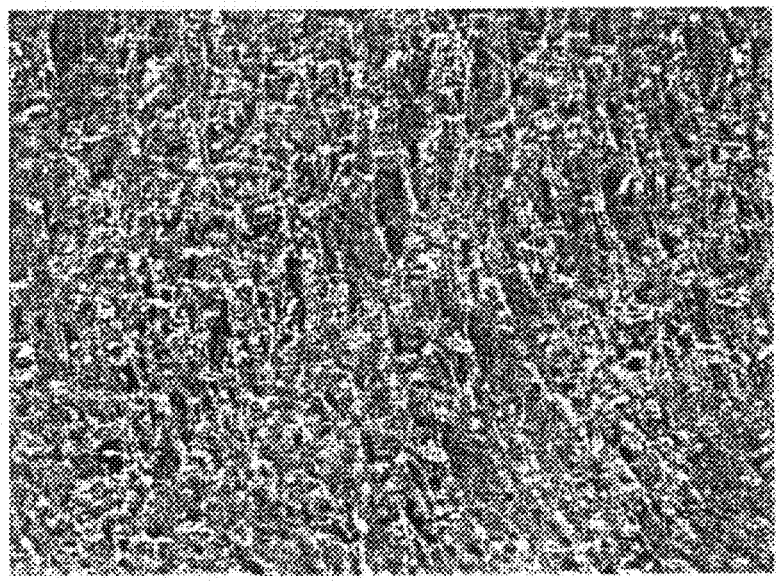
FIG. 3 shows a light photomicrograph of interconnected porous chitosan wound dressing structure sectioned normal to base.
Figure 4:
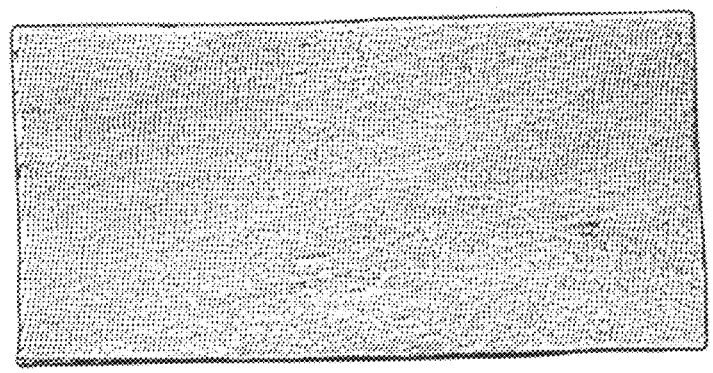
FIG. 4 shows a Photograph of chitosan biomaterial wound dressing after heating and compression.
Figure 5:
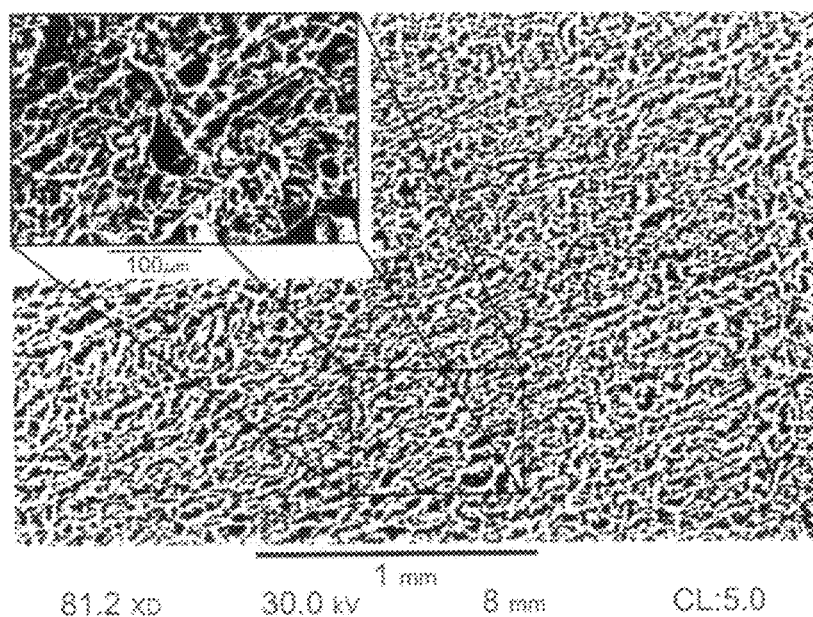
FIG. 5 shows a scanning electron photomicrograph of a typical base surface of compressed chitosan wound dressing. Higher magnification inset (bar=100 micron).

Wound dressings were prepared from the 2% aqueous solutions of chitosan that were poured into Teflon'"-coated aluminum or polystyrene molds to at least 1.5 em deep and frozen in a −80° C. Revco freezer at −45° C. for 3 hours. Alternatively, freezing was carried out on the shelves inside a Virtis Genesis 35EL freeze drier. There was at most 10% shrinkage in the wound dressings and the final freeze-dried wound dressing density was near 0.033 g/cm3. Transverse cross sections of two types of molded wound dressings are shown in FIGS. 1 & 2 (different freezing rates). The structures observed (FIG. 3) were affected by the rates of cooling in the hulk solution and at the different surfaces. Subsequently, structures in the wound dressings were controlled by formulation, mold (size & shape) and freezing conditions. Optimal wound dressing structures were those that were open-porous consisting of uniform interconnected pores of close to 50 microns in diameter or lamella and hexagonal structures normal to the plane of cooling. These structures could be controlled, yielding flexible yet strong wound dressings of large specific surface areas for highly efficient and rapid blood coagulation. Typically, the available specific surface area for such structures was greater than 500 cm$^2$/g. The scanning electron photomicrograph in FIG. 5 shows the typical open cell structure in the base surface of a wound dressing. The wound dressings were heated in a convection oven at 80±1° C. for one half hour to optimize the structure and distribution of acetic acid concentration. It was found that this step was essential to optimize the adhesive properties of the wound dressing in a bleeding field (typically adhesion to dermis>40 kPa). The wound dressings were immediately compressed from 17 mm thickness to 5.5±0.5 mm at 80±5° C. under a loading of close to 50 kPa (from ca. density 0.03±0.005 g/cm$^3$ to 0.12±0.02 g/cm$^3$). FIG. 4 shows the appearance of the base of a typical preferred chitosan wound dressing for hemorrhage control after heating and compression.

Example 2

Preparation and Evaluation of Wound Dressing

Hemostatic wound dressings were prepared as follows:

a) Dry chitosan powder or flake with degree of deactylation above 85%, less than 26 ppm metallic component and greater than 90% dry solids content was made in a 2% aqueous solution (w/w) with about 2 or 1% acetic acid (w/w) at 40° C.

b) The solution of chitosan from a) above was degassed under reduced pressure at up to about 500 mTorr under agitation for at least 5 minutes and poured into a mold to a depth of 1.7 cm. Certain low-density, foam structures exhibited problems due to their ready dissolution in a bleeding field. These problems were generally avoided by thorough degassing of the solution.

c) The mould containing the degassed chitosan solution was frozen by cooling from room temperature to −45° C. A linear cooling ramp was used over a 90 minute period, and the temperature was maintained at −45° C. for at least another hour.

d) The frozen chitosan was then freeze dried using a condenser which was at a temperature below −70° C. and a vacuum at about 100 mTorr. The shelf temperature was ramped from −45° C. to −15° C. and held at that level for 10 hours. A further 36-48 hours of freeze drying at 10° C. was then performed. Freeze drying was performed until achieving close to about 2.8% of the original frozen plaque mass.

e) At 2.8% of original mass, the process was stopped, and the freeze dried wound dressing removed from the mold.

f) The product formed was an acid buffered, water soluble, high specific surface area wound dressing that had shrunk 10% from its original frozen volume. The wound dressing structure was generally a uniform open porous structure with 50 to 80 micron diameter interconnecting pores. Using a slightly different cooling regime in which super-cooling was not affected, a lamella/hexagonal structure (with uniformly thin chitosan sheets close to 5 microns thick with close to 50 microns separation between sheets) was achieved.

g) The wound dressing was then compressed (from 1.7 cm to ca. 0.5 cm thick) between smooth and flat platens heated to 80±2° C. under application of 60±20 kPa pressure.

h) Next, the dressing was conditioned in a convection oven by heating at 80±5° C. for 30 minutes.

i) Each wound dressing was then stored in labeled Kapak 530 heat sealed pouches.

j) The resultant pressed wound dressing was tough, flexible, hemostatic, adherent to wet tissue and resistant to dissolution by streaming blood.

k) Improved dissolution properties, improved adhesion strength and sterilization were achieved by exposure of the wound dressing to 15 kGy gamma irradiation under nitrogen atmosphere.

In vivo evaluation of hemostasis of candidate hemorrhage control dressings of varying composition and structure was screened in increasingly challenging animal models of hemorrhage. A spleen laceration model was utilized in order to be able to screen large numbers of candidate dressings in a simple reproducible model and to compare them to conventional materials. Although this is the least challenging bleeding model (mild oozing bleeding ca. 2-5 mL/min), most initial wound dressing formulations failed this test. Also all chitosan gels, powders failed in this test while films performed poorly.

Prior to testing in a severe hemorrhage model, swine were anticoagulated with systemic intravenous heparin and better materials were tested in a capsulated spleen stripping model (strong oozing bleeding ca. 10-20 mL/min). Those few materials that passed this test were then evaluated in the carotid laceration model (ca. 50 mL/min) in anticoagulated swine. Wound dressing formulations of candidate materials passing this test were then tested on the swine aortotomy model with in which 4 mm diameter perforations in were made in the thoracic or abdominal aortas. Materials passing these challenging models of severe vascular hemorrhage (bleeding rates in excess of 100 mL/min) were also tested in a severe (Grade V) model of hepatic trauma.

The testing was carried out on healthy animals that had previously undergone procedures and were scheduled to be sacrificed for evaluation. All experiments were performed in accordance with the 1996 National Research Council, "Guide for the Care and Use of Laboratory Animal" and applicable Federal regulations. After identification of the animal, anesthesia was induced with Telazol 4-9 mg/kg intramuscularly (i.m.). Isoflurane was given by mask and the animal was intubated.

The chitosan patches for the laceration and capsular stripping experiments were either equal size quarter pieces cut from a 37 mm diameter wound dressing or 1.5 cm×1.5 cm wound dressing pieces cut from a larger wound dressing.

Control materials of Gelfoam™+thrombin or Surgicel™ were prepared from 1.5 cm×1.5 cm pieces. Gelfoam™ size 100, absorbable gelatin wound dressing, was supplied by Pharmacia. Oxidized cellulose, Surgicel"1, was supplied by Ethicon. Topical thrombin (bovine origin) 10,000 U.S. units was supplied by Jones Pharma. The Gelfoam™+thrombin was prepared before use by soaking of 1.5 cm×1.5 cm×0.8 cm wound dressings in the thrombin for 30 minutes.

A midline ventral laporatomy was performed. The top half of the spleen was exteriorized (apposing the surgical wound with towel clamps). The surface was kept moist by the application of sterile saline solution from a wet lap pad.

For anticoagulation, the right femoral artery was surgically isolated and cannulated with a 6F sheath, allowing for collecting blood samples. The activated clotting time (ACT) was measured before administration of 5000 units of heparin intravenously, 10 minutes after administration of heparin and every 20 minutes thereafter. If the ACT level was less than 200 seconds, 2000 units of heparin were given and the ACT was remeasured after 10 minutes. This was repeated until the ACT>200 seconds to ensure that the animal was anticoagulated.

The area of splenic testing was demarcated and kept moist by using the towel clamps and wet pads and only exposing the most immediate untested surface. A single injury was made prior to the application of a test patch, as follows:

i) In the laceration model, the injury (8 mm long×4 mm deep) was made using a #11 surgical blade positioned in a right-angled forceps so that 4 mm of blade was protruding.

ii) In the capsular stripping model, the injury (5 mm×5 mm×4 mm deep) was made using the clamped #11 blade and a pair of surgical scissors.

After making the injury, bleeding was allowed for 30 seconds. The surface blood was removed with gauze, following which a test patch was applied digitally to the injury using a constant uniform pressure for 30 seconds. The digital pressure was then removed and the patch was observed for two minutes. At this stage, the trial number was recorded. If observable rebleeding occurred, the time to rebleed was recorded, and the next trial (30 second bleed, clean away blood with gauze, 30 seconds digital pressure followed by up to 2 minutes observation) commenced. The trial for a test patch was complete when no rebleeding occurred in the 2 minute observation period or if 6 trial rebleeds were observed. If the wound continued to rebleed for 6 trial periods, then the failed patch was removed and a Gelfoam+thrombin patch applied. A new injury was made and another patch tested.

In the case of the carotid laceration model, chitosan patches (37 mm×25 mm) were cut from the 37 mm diameter compressed wound dressing or larger wound dressings. For facility in application, some of the wound dressings had a top layer of 3M 9781 foam medical tape attached to the chitosan with 3M 9942 skin adhesive. Gelfoam™+thrombin was used as a control.

A vertical incision was made exposing a 10 cm length of carotid artery. The fascia was retracted and the surrounding soft tissue was dissected until the artery was supported on a flat base of tissue. Tie-off sutures were placed proximal and distal to the exposed artery. These were clamped and a 1.5 cm incision was made longitudinally in the artery.

For anticoagulation, the right femoral artery was surgically isolated and cannulated with a 6F sheath, allowing for collecting blood samples. The activated clotting time (ACT) was measured before administration of 5000 units of heparin intravenously, 10 minutes after administration of heparin and every 20 minutes thereafter. If the ACT level was less than 200 seconds, 2000 units of heparin were given and the ACT was remeasured after 10 minutes. This was repeated until the ACT >200 seconds to ensure that the animal was anticoagulated.

After making the incision, the artery was allowed to bleed for 2 seconds and then was compressed for 1 minute. The compression was removed and the ties were re-clamped. The area was flushed with saline. The ties were unclamped 2 seconds before application of a patch. Pressure was applied uniformly over the patch for 3 minutes. If bleeding was observed within 30 minutes after application of pressure, then another 3 minutes of pressure was re-applied. If the patch was not adhering then it was replaced with a new patch. Each re-application of pressure, or replacement of a patch of the same type were treated as trial periods for that patch type. A trial for a particular wound dressing was considered complete if no bleeding was observed from around, or through the patch in a 30 minute period. A material was rated on the number of trials it took to achieve 30 minutes of hemostasis (no observable bleeding from the wound).

In the case of swine aorta perforation, sample patches of compressed chitosan wound dressing cut to 2.5 cm diameter pieces or controls of 4"×4" surgical gauze were used.

Either or both the abdominal and the thoracic aortas were exposed by midline ventral laporatomies in the former and sternotomies in the latter. The fascia and sternum were clamped and ties were placed proximal and distal to the sites of incision. While the tie-off clamps were applied, a #11 scalpel blade was used to make a 3 mm incision through the wall of the aorta and a 4 mm diameter Medtronic~' vascular punch was inserted through the incision to make a 4 mm diameter hole in the aorta. The punch was removed and the tie-off clamps released with digital pressure applied to the hole.

The patch was held between thumb and forefinger with the middle finger applying pressure to the hole in the aorta. The pressure from this middle finger was released for I second before application of the wound dressing to the bleeding field. The wound dressing was held in place by firm pressure applied through the forefinger to the patch over the aortic hole. The pooled blood that escaped the wound during application of the patch was suctioned away. After 3 minutes of digital pressure, the finger was removed and the patch observed for any sign of continued bleeding and poor adherence.

If continued bleeding or re-bleeding was observed in the first 30 minutes after application of the patch, then a further 3 minutes of pressure was applied. If hemostasis was still not complete, then another patch of the same wound dressing was prepared, the old patch removed and a new trial commenced. A trial was considered complete if no bleeding was observed from around or through the patch in a 30-minute period. A material was rated on the number of trials it took to achieve 30 minutes of hemostasis (no observable bleeding from the wound). Control samples of gauze were applied in the same manner as the chitosan wound dressing during a trial.

All animals were euthanized while under anesthesia with an injection of barbiturates (Euthasol, 1 mL/10 lb) via an auricular vein. Animals were euthanized at the end of the experimental procedure or prior to the end if the animal experienced any untoward effects.

Tests were ranked from 0.0 to 6.0 according to the number of trials necessary before hemorrhage control was achieved and the time to rebleed (only in the case of the spleen trials). A test in which only one trial was necessary and there was no rebleed was ranked as 0.0. A test which required a second trial and the time to rebleed of the first was 90 seconds was ranked:

$$1.0 = (120-90/120) = 1.25$$

(in the case of a spleen) or 1.0 in the other models.

A test which needed four trials to achieve hemostasis and where the time to splenic rebleed in the third trial was 30 seconds was ranked:

$$3.0 + (120-30/120) = 3.75$$

(in the case of a spleen) or 3.0 in the other models.

A sample that failed completely by rapid dissolution, lack of adherence or uncontrolled bleeding was ranked 6.0+.
In summary, the worse the hemostasis, the higher the ranking as defined by the following:

$$R = G + A$$

Where G=number of trials to stop bleeding−1

$$A = \frac{A - \text{time to rebleed}(s) \text{ in previous trial}}{A}$$

A=time of trial (s)

The results of the spleen studies are summarized in Tables 2, 3 and 4. Table 2 illustrates the behavior of chitosan test samples that were non-optimized with respect to composition and structure. These non-optimized materials ranged from, worse to the Surgicel™ negative control (Table 4), to comparable and to only partially better. The presence of phosphate buffer solution produced a poorly adherent, slowly hemostatic patch that was only slightly more effective than Surgicel™. The chitosan film was moderately adherent, providing a reasonable seal to bleeding, however it was only very slowly hemostatic as evidenced by the slow welling of blood beneath its transparent surface. The earlier trials generally showed signs of a low density foam in the top surface of the molded wound dressing. It was found that this low density foam was susceptible to dissolution and collapse if the top surface of the wound dressing was applied to a bleeding field. It was subsequently discovered that this foam effect could be avoided by degassing of solutions before freezing. Low molecular weight chitosan wound dressings (relative 1% solution viscosity <50 cps) were found to be very susceptible to dissolution in a bleeding field making them unsuitable for the patch application. The glutamate counter anion produced softer wound dressings but at the cost of producing wound dressings that were readily dissolved in a severely bleeding field. Low density wound dressings (those less than 0.05 g/cm3) with acetate counterions were also found to be readily compromised by dissolution and collapse.

Table 3 shows the result rankings of the optimized chitosan wound dressings of preferred composition and structure. These wound dressings were composed of chitosan with higher molecular weights (relative 1% solution viscosity greater than 100 cps) and had wound dressing densities close to 0.12 g/cm$^3$. In the moderately bleeding spleen tests, the results for the optimized wound dressings were found, using a Wilcoxon Rank Sum W Test, to be indistinguishable from the positive control of Gelfoam™+thrombin (Z=−0.527, = 0.598). Using the same statistical method, the wound dressings were shown to be significantly different from the poorly performed Surgicel™ control Z=−3.96, p=0.0001).

Figure 6:
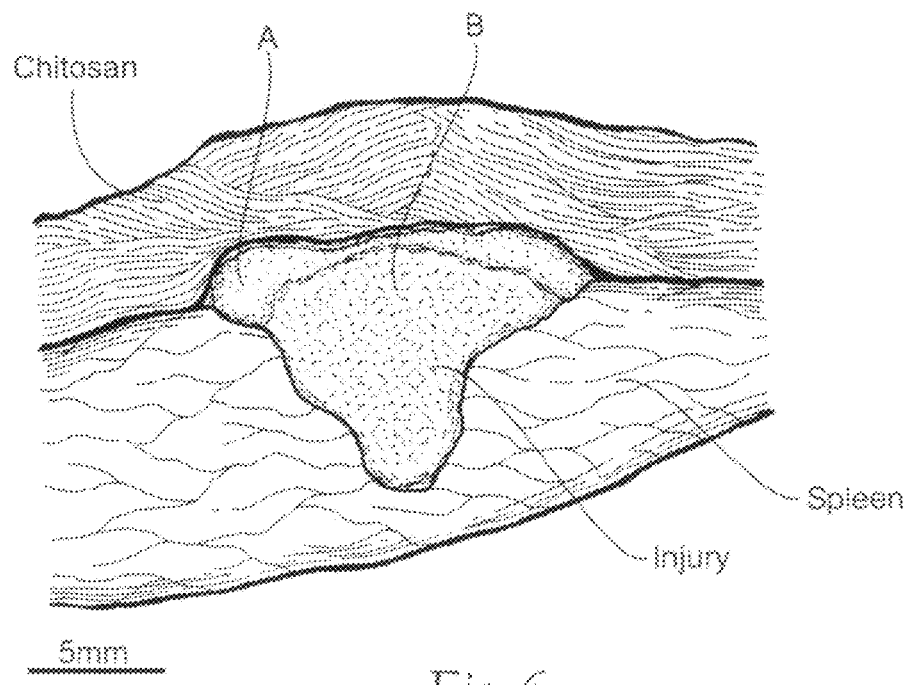
FIG. 6 shows a histological stained section through chitosan/spleen injury site and adjacent splenic surface. Agglutinated clot response (A) with a mixture of fibrin/platelet rich blood clot (B) between patch and spleen. The figure demonstrates very good adhesion between spleen and chitosan.

FIG. 6 demonstrates (via a H&E stained histological section) the close adherence of the optimized chitosan wound dressings patches to the spleen surface as well as the agglutination of erythrocytes at the immediate vicinity of the injury.

The rankings for the carotid injury model are summarized in Table 5. In this model, the optimized chitosan patch performed very well in trials 3, 5 and 6. The improvement in performance over the first trials 1 and 2 was due to the application of the support hacking (3M 9781 foam bandage) to the immediate top surface of the wound dressing. This backing enabled more uniform pressure to be applied over the wound dressing and allowed for the person applying the dressing to remove their fingers easily from the patch surface without them sticking and inducing patch detachment from the wound. The carotid model was used to investigate more severe arterial bleeding conditions than were possible in the spleen injury model. Gelfoam™+thrombin was investigated as a possible positive control but was found to dissolve in a highly bleeding field.

Figure 7:
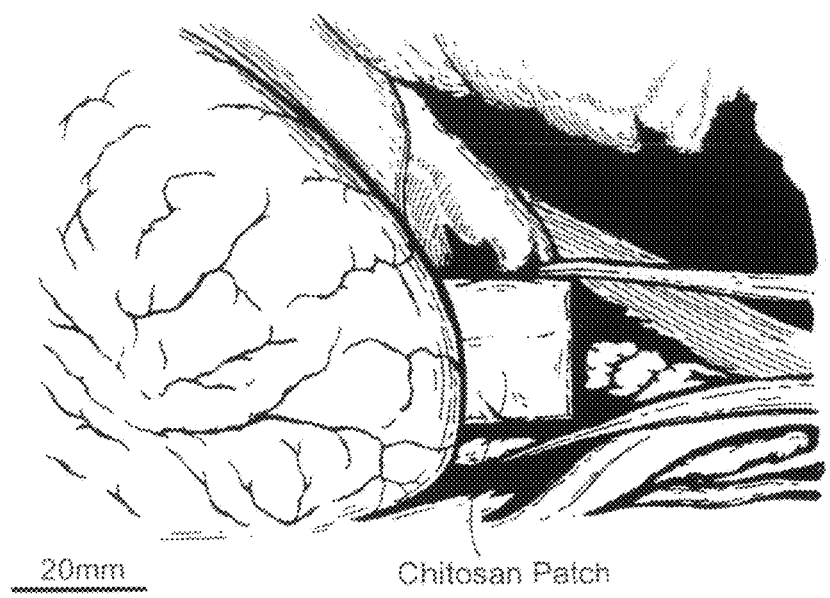
FIG. 7 shows a photograph of thoracic aorta injury sealed with chitosan patch.
Figure 8:
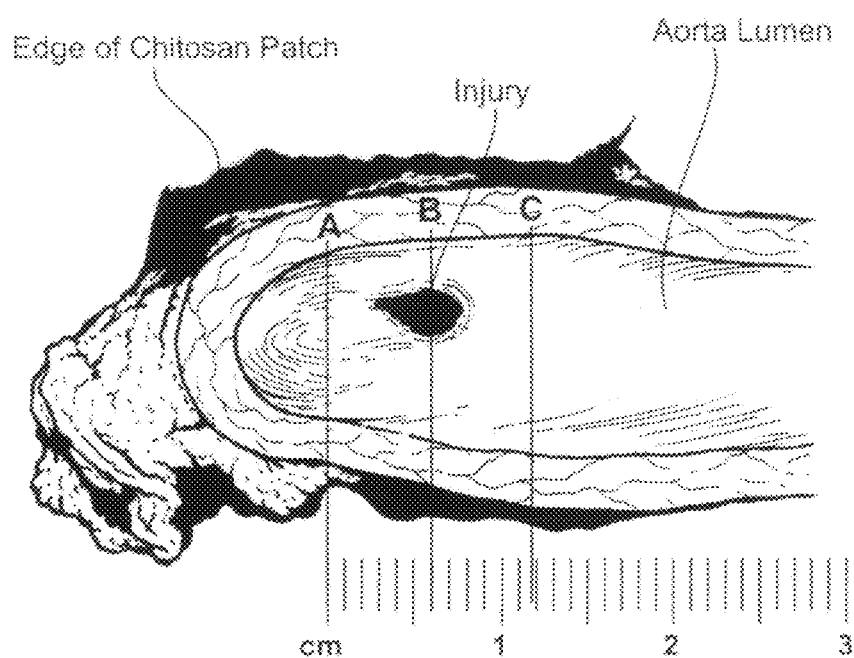
FIG. 8 shows a fixed thoracic aorta demonstrating perforation injury.
Figure 9:
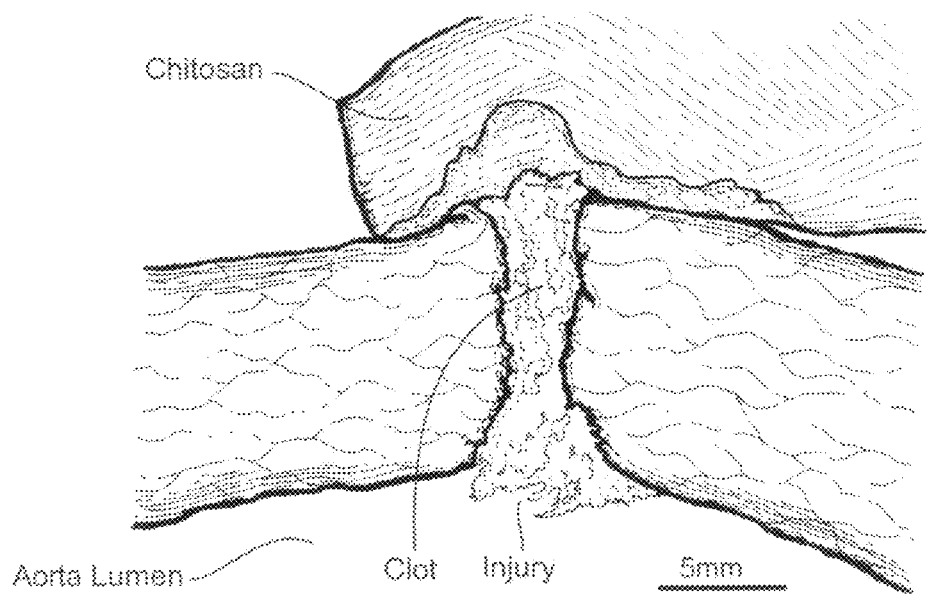
FIG. 9 shows a stained histological section through thoracic aorta injury.

Table 6 summarizes the results of the aortic injury model. Gauze bandage (4"×4") was used as a control bandage. It was found that the control was unable to stop severe bleeding in all trial periods whereas the optimized chitosan aortic patches were able quickly to stop and subsequently clot the very high level of bleeding observed in this wound after only 1 or 2 applications of the patch. The exact significance (two-tailed p=O.OO2) was determined for the probability that there was no difference between rankings of sample and control. On average the blood loss after patch application was minimal (<50 mL) if the wound was stanched on the first attempt. If a second attempt was required blood loss after patch application was greater than 100 mL but less than 300 mL. On average less than 150 mL of blood was lost after patch application in the case of the chitosan wound dressing while, in the case of the 3 gauze control studies, more than 1 liter of blood was lost for each animal. In the case of the chitosan wound dressing study, survival was 100%, while in the case of the gauze study, none (0%) of the animals survived. The chitosan patches demonstrated continued hemostatic efficacy over the trial period of 30 minutes and until the animals were sacrificed which was generally 1 to 2 hours later. FIG. 7 demonstrates a typical chitosan patch sealing a severe thoracic wound. The lumen side (showing the injury) of the resected aorta sealed by the patch in FIG. 7 is shown in FIG. 8. FIG. 9 shows a photomicrograph of a stained histological section taken through the injury of FIGS. 7 & 8. Evidence of strong clotting at the injury site was found on removal and inspection of aortas on animal sacrifice (FIG. 9) and, in the case of trial number 16, where after dislodging a patch in a live animal (after more than 30 minutes of application) there was no subsequent re-bleeding.

Example 3

Hepatic Hemorrhage Control in Swine Liver Model

The US Army Science and Technology Objective (STO) A, Hemorrhage Control, was established in 2000 to advance the need for hemorrhage control on the battlefield. The general strategic objective of the STO can be summarized as the development of products and methods that will reduce the number of deaths due to hemorrhage in battlefield casualties. The requirements for hemorrhage control products and methods were stated thus:

They must be practicable for use by one or more of the following: self (wounded combatant), buddy (fellow non-medical soldier who aids the wounded soldier), combat lifesaver, combat medic, physician assistant, and battalion surgeon. They must be practicable for use in far forward field conditions including rugged terrain, limited visibility, and environmental extremes. Products and methods must not require external electrical sources. All devices must be man-portable and durable. It is expected that products and methods that are useable far forward will also be used at higher echelons of care. A specific strategic objective of the STO is the development of new or improved hemostatic agents for use on compressible hemorrhage under far forward field conditions. A single product for use on compressible and non-compressible sites is desired.

As part of STO, a study of hepatic hemorrhage control in a swine liver model was conducted at the US-Army Institute of Surgical Research (ISR) at Fort Sam Houston, San Antonio, Tex. using the hemorrhage control bandage of this invention. The study was conducted to determine the effect of the chitosan hemorrhage control bandage on blood loss and survival in a standardized model of severe venous hemorrhage and hepatic injury in swine. This model has been used to study numerous other hemostatic bandages at US-Army ISR.

Cross-bred commercial swine were used in this study. Animals were maintained in a facility accredited by the Association for the Assessment and Accreditation of Laboratory Animal Care, International. This study was approved by the Institutional Animal Care and Use Committee of the U.S. Army Institute of Surgical Research, Fort Sam Houston, Tex. Animals received humane care in accordance with the Guide for the Care and Use of Laboratory Animals (National Institutes of Health publication 86-23, revised 1996).

Animals were assigned randomly to receive either the Chitosan bandages or Gauze sponges (see Table 7). Surgical preparation consisted of the following: Animals were fasted 36-48 hours prior to the surgical procedure, with water allowed ad libitum. After premedication with glycopyrrolate and a combination of tiletamine HCl and zolazepam HC1 (Telazol®, Fort Dodge Laboratories, Fort Dodge, Iowa), anesthesia was induced by mask using 5% isoflurane. The swine were intubated, placed on a ventilator, and maintained with isoflurane. Carotid arterial and jugular venous catheters were placed surgically. Laparotomy was performed and splenectomy and urinary bladder catheter placement were completed. A rectal temperature between 37.0° C. and 390° C., and 15 minutes of stable mean arterial pressures (MAP) were required prior to further experimental procedures. Blood pressure and heart rate were recorded at 10-second intervals throughout the study period using a continuous data collection system (Micro-Med®, Louisville, Ky.). Baseline arterial blood samples were collected from each animal to confirm that each animal exhibited normal platelet count, prothrombin time, activated partial thromboplastin time, and plasma fibrinogen concentration.

Liver injuries were induced. The method included the following. The liver was retracted by manually elevating the left and right medial lobes to allow adequate exposure. Next, a specially designed clamp with two 4.5 cm sharpened tines configured in the form of an 'X' was positioned with the center approximately 2-3 cm dorsal to the intersection of the left and right medial lobes, on the diaphragmatic surface of the liver. The base plate of the instrument was positioned beneath the quadrate lobe, on the visceral surface. The injury was induced by clamping the tines of the instrument through the parenchyma and underlying vessels of the two medial lobes so that the tines were seated in corresponding grooves in the base plate of the instrument. After the first penetration of the liver, the instrument was opened and the tines were withdrawn and repositioned to the animals left such that the second application would overlap the first by 50 percent. Following this repositioning, the liver was penetrated a second time. Documentation of the liver injury was achieved by excision and inspection of the liver at the conclusion of the experimental period. The injuries appeared as large stellate wounds with a small island of tissue in the center, and measured approximately 10×8×4 cm. The injuries were through and through, with one or more of the left medial lobar vein, right medial lobar vein, and portal hepatic vein lacerated.

Thirty seconds after injury, resuscitation was initiated with warm (38° C.) lactated Ringer's solution in all animals. The goal of resuscitation was return to baseline MAP. Fluid was administered at 260 mL/min. This resuscitation regimen was continued until the goal was reached and reinitiated if MAP decreased, throughout the 60 minute study period. Simultaneously with initiation of resuscitation (30 seconds post-injury), treatments were applied as follows. One dressing was applied to the surface of the quadrate lobe to cover the penetrating injury and two other dressings were stuffed into the injury from the diaphragmatic aspect. Compression was applied for 60 seconds in the dorso-ventral direction. After 60 seconds, the injury was inspected to determine whether hemostasis was achieved. Next, the applicator's hands were repositioned and pressure was applied for 60 seconds in the latero-medial direction, and the observation for hemostasis was performed. This sequence was repeated for a total of four 60 second compressions. If hemostasis was complete after any compression, no further compressions were performed. Hemostasis was defined as the absence of visually detectable bleeding from the injury site.

Following completion of treatment application, the abdomen was closed and the animal was monitored for 60 minutes after injury or until death, whichever came first. Death prior to 60 minutes was defined as a heart rate of 0. At 60 minutes, surviving animals were euthanized by an overdose of pentobarbital.

Immediately after induction of the injury, blood was continuously suctioned from the peritoneal cavity until the start of treatment application. The volume was determined and designated as pre-treatment blood loss. At the end of the study period, each abdomen was opened and the liquid and clotted intra-peritoneal blood were suctioned and measured. This was designated as post-treatment blood loss. Additionally, total resuscitation fluid use was recorded. Pre-injury animal blood volume was estimated as previously reported (Pusateri et al, Mil Med. 166, 217-222, (2001)).

Body weight, estimated blood volume, number of vessels lacerated, baseline MAP, survival time, preinjury MAP, pre-treatment blood loss, and bandage adherence scores were analyzed by analysis of variance using the GLM procedure of SAS. Data are reported as least squares mean±standard error of least squares mean. Data were examined for heterogeneity of variance and non-normality. These conditions were detected for post-treatment blood loss and fluid use data. Therefore, blood loss and fluid use data were log transformed prior to analysis. The transformed data were analyzed by analysis of variance. These data are expressed as back transformed means and 95% confidence interval (95% CI). Distribution of females and males, hemostasis, and survival data were analyzed by Fishers Exact Test using the FREQ procedure of SAS. Data are reported as proportions or percentages. Two sided tests were used for all comparisons.

There were no differences among treatment groups in animal body weight, estimated blood volume, distribution of animal sexes, baseline MAP, preinjury MAP, number of major vessels lacerated within the liver injury, or pretreatment blood loss (See Tables 8 and 9).

Post-treatment blood loss was reduced in the Chitosan group, compared to the Gauze wound dressing control (p=0.01). No significant difference in fluid use was observed. Survival percentage was increased in the Chitosan group (p=0.04). Hemostasis occurred more frequently in the Chitosan group at 3 and 4 minutes post-injury (p=0.03). Survival times could not be statistically compared because of the high level of survival in the Chitosan group (See Table 10).

TABLE 7

| Test Material | Lot Number and Related Information |
| --- | --- |
| Gauze Dressing (Negative Control) | Johnson and Johnson NU Gauze Sponge General Use 10.2 cm × 10.2 cm. Rayon/Polyester Formed Fabric. Lot Number 1999-05 1399T5205B2. |
| Chitosan Wound Dressing | Oregon Medical Laser Center, Chitosan Wound dressing, 10.2 cm × 10.2 cm. Lot Number 052101. Batch Number E1041. 26 May 2001 (1% AA, Priniex - Lot#751). |

TABLE 8

| Variable | Gauze Sponge Control Group | Chitosan Group | P value of difference |
| --- | --- | --- | --- |
| N | 7 | 8 | N/A |
| Body Weight (kg) | 39.1 ± 1.2 | 38.7 ± 1/1 | 0.82 |
| Estimated Blood Volume (mL) | 2819 ± 66 | 2800 ± 64 | 0.83 |
| Female/Male (n/n) | 5/2 | 6/2 | 0.88 |
| Baseline MAP (mmHg) | 71.3 ± 3.6 | 68.8 ± 3.3 | 0.50 |
| Preinjury MAP (mmHg) | 69.1 ± 4.8 | 69.3 ± 4.4 | 0.98 |
| Hematocrit (5) | 32.2 ± 1.1 | 32.6 ± 1.0 | 0.79 |

TABLE 8-continued

| Variable | Gauze Sponge Control Group | Chitosan Group | P value of difference |
|---|---|---|---|
| Hemoglobin (g/dL) | 11.2 ± 0.4 | 11.3 ± 0.3 | 0.80 |
| Platelets (1000/μl) | 567 ± 28 | 502 ± 25 | 0.11 |
| PT (sec) | 10.7 ± 0.2 | 10.6 ± 0.2 | 0.70 |
| APTT (sec) | 15.7 ± 0.9 | 16.5 ± 0.9 | 0.56 |
| Fibrinogen (g/dL) | 159 ± 0.9 | 180 ± 8 | 0.10 |

TABLE 9

| Variable | Gauze Sponge Control Group | Chitosan Group | P value of difference |
|---|---|---|---|
| Number of Vessels Lacerated | 1.86 ± 0.29 | 1.88 ± 0.27 | 0.96 |
| Pretreatment Blood Loss (mL) | 296.1 ± 55.4 | 291.1 ± 55.4 | 0.95 |
| Pretreatment Blood Loss (mL/kg body weight) | 10.6 ± 2.0 | 10.3 ± 2.0 | 0.94 |

TABLE 10

| Variable | Gauze Sponge Control Group | Chitosan Group | P value of difference |
|---|---|---|---|
| Post-treatment Blood Loss (mL) | 2879 (788-10.513; 95% CI) | 264 (82-852; 95% CI) | <0.01 |
| Post-Treatment Blood Loss (mL/kg body weight) | 102.4 (28.2-371.8) | 9.4 (2.9-30.3; 95% CI) | <0.01 |
| Fluid Use (mL) | 6614 (2,519-17,363; (95% CI) | 1793 (749-4,291; 95% CI) | 0.03 |
| Survival (5) | 28.6 | 87.5 | 0.04 |
| Survival Time (min; nonsurvivors only) | 38.4 ± 5.8 (n = 5) | 10.0 (n = 1) | N/A |
| Hemostasis at 1 min (5) | 0 | 50 | 0.08 |
| Hemostasis at 2 min (5) | 0 | 50 | 0.08 |
| Hemostasis at 3 min (5) | 0 | 62 | 0.03 |
| Hemostasis at 4 min (5) | 0 | 62 | 0.03 |

This US-Army ISR study (Pusateri et al. J. Trauma, 54, 177-182, (2003)) demonstrates, in an independent study, the significantly improved performance of the chitosan wound dressing over standard 4"×4" gauze. The US-Army ISR has only been able to demonstrate significantly improved performance over 4"×4" gauze in the stanching of severe blood flow in the case of the dressing of this invention claim and in the case of a dry Fibrin Thrombin wound dressing being developed by the Red Cross. The Red Cross Bandage is costly, as well as being delicate and prone to breakage.

Example 4

Irradiation of Bandages

High molecular weight 4"×4" chitosan hemorrhage control dressings with 3M 9781 porous foam backing were prepared from an Icelandic shrimp source (Genis Lot# SO1115-1). These were prepared with 2% acetic acid and 2% chitosan solution using a commercial freeze drying company to prepare a large sterile lot of chitosan bandages (Lot#OMLC__2SM114). The bandages were irradiated at 15 kGy under nitrogen. They were subsequently tested for uniaxial tensile strength, burst strength, blood adsorption, water adsorption as well as for sterility. Swine aorta perforations were carried out on non-gamma irradiated samples in abdominal and thoracic injuries. Seven patches were used. On average blood loss after patch application was <50 mL. All patches were adherent, wound sealing and hemostatic on their first application (7× 0rankings). All animals survived.

Both gamma-irradiated and un-irradiated bandages (Lot#OMLC__2SM114) were tested with an in vitro burst pressure test developed at Oregon Medical Laser Center in Portland Oreg. To perform a burst test, a 25 mm diameter circular test piece of the bandage is immersed in citrated whole blood for 10 seconds. The test piece is then placed centrally over, and firmly held with digital pressure, on a 4 mm diameter perforation in the side of a 50 mm diameter PVC pipe for 3 minutes. After this initial attachment, fluid pressure inside the pipe is ramped at $4.5 \pm 0.5$ kPa·s$^{-1}$, with pressure and time recorded at 0.1 second intervals. Burst pressure is recorded as the maximum pressure recorded prior to failure. An adhesive failure ranking is assigned to assess the relative adhesiveness of the bandage to the test site. The ranking system is separated into 3 distinct modes of failure. A ranking of 1 is given to a test piece that is readily separated from the PVC surface with no chitosan remaining adhered. A ranking of 2 is assigned when the test piece is less readily detached and some of the chitosan remains attached to the test site. A ranking 3 is assigned when the test piece can only be removed by cohesive separation of the bulk wound dressing from the base structure which remains firmly fixed to the PVC surface.

Figure 10:
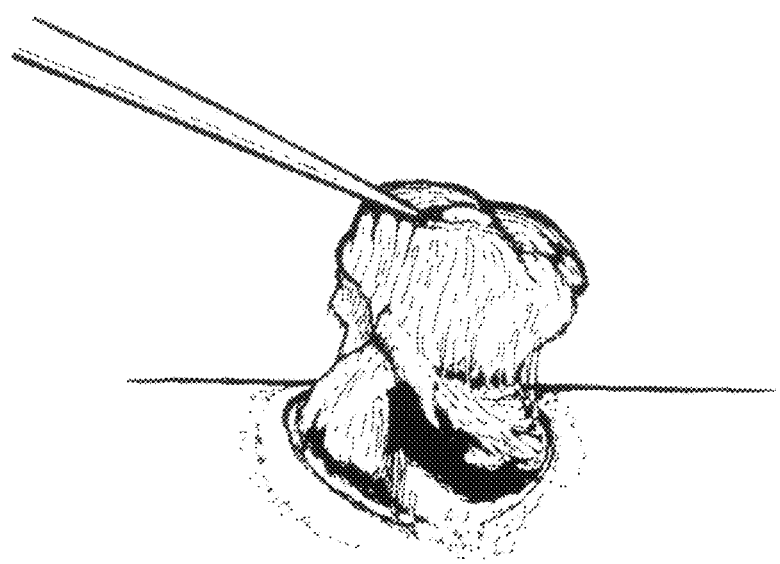
FIG. 10 shows a photograph of in vitro burst pressure failure in a strongly adherent dressing.

The average burst pressure of gamma irradiated and un-irradiated chitosan bandages (Mean±SD, n=6) on a PVC substrate using blood as wetting medium was 122±1.9 kPa and 86±20 kPa, respectively. The results were analyzed statistically using a T-test (p=0.007). The average adhesive failure rankings of gamma irradiated and un-irradiated chitosan alpha bandages (Mean±SD, n=6) on a PVC substrate using blood as wetting medium were both 3±0. FIG. 10 shows an image of a high ranking failure where cohesive failure has occurred within the chitosan structure.

Figure 11:
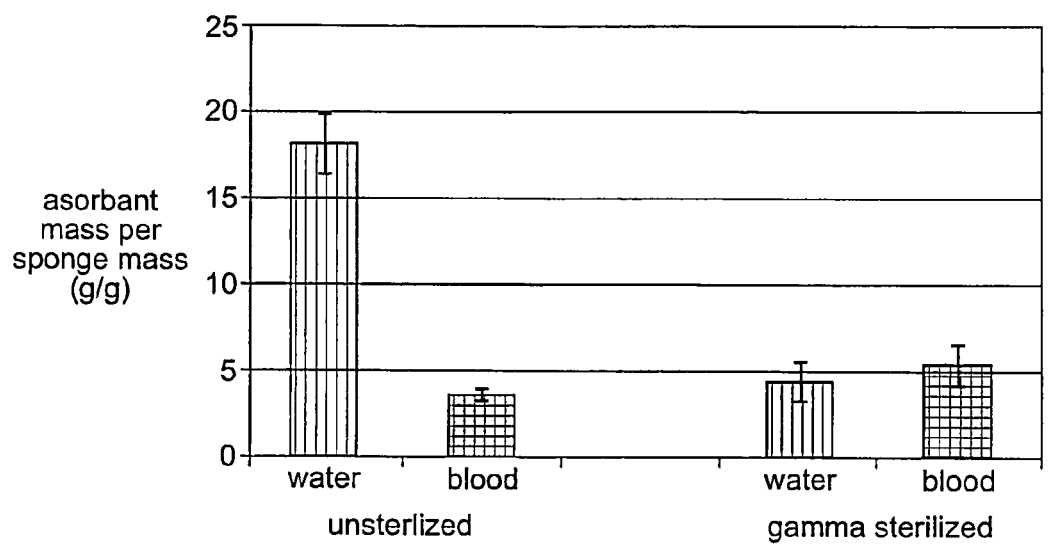
FIG. 11 shows a histogram of water and blood adsorption results for gamma irradiated and un-irradiated (i.e., unsterilized) samples.

The blood and water adsorption properties of the dressings (Lot#OMLC__2SM114) were determined by immersing small test pieces (ca. 0.02 g) in blood or water for 3.0 seconds. Difference in mass before and after immersion was recorded. The average mass of medium adsorbed in 3 seconds per one gram of wound dressing was determined for gamma irradiated and un-irradiated chitosan samples (n=4) using blood or water as the wetting medium (see FIG. 11). The results were analyzed statistically using a one-way ANOVA with a Tukey-HSD test, p=0.001. Gamma irradiation significantly reduced the excessive adsorption of water in the case of the non-irradiated material. Such excessive water adsorption would cause wound dressing collapse (into a gel) with subsequent adhesive and structural failure.

Tensile test pieces of the chitosan dressings (Lot#OMLC__25M114) were evaluated using a uniaxial Chatillon Materials Testing Vitrodyne V1000 equipped with a 5 kg load cell. Samples were cut into dog-hone pieces (15±1 mm×6.5±0.5 mm×5±0.5 mm gauge×thickness×width) and held between two clamps. The crosshead speed was 10 mm·s$^{-1}$. Load and displacement were recorded at 0.1 second intervals.

Tensile results of whole dressings are shown in Table 11. There were no significant differences between gamma irradiated and un-irradiated samples with respect to both stress and strain. There was a small increase in Youngs modulus with irradiation at 15 kGy.

TABLE 11

| Sample | Youngs Modulus (Mpa) | Ultimate Load* (kg) | Ultimate Elongation |
|---|---|---|---|
| No irradiation (n = 5) | 1.8 ± 1.2 | 2.2 ± 0.2 | 0.9 ± 0.1 |
| Gamma irradiation (n = 9) | 4.4 ± 2.7 | 2.3 ± 0.2 | 0.85 ± 0.15 |

*Calculated for a 2.5 cm wide bandage

Fifty two 4"×4" chitosan wound dressings (Lot#OMLC 2SMI 14) were prepared cleanly. Of these 4"×4" wound dressings, 46 were packaged in a double pack envelope and were sent to the IsoMedix facility in Ontario, Calif. for irradiation with gamma radiation at a certified dose between 14-15 kGy. Boxed with these samples were a set of 8 *Staphylococcus aureus* (ATCC 29213) doped chitosan wound dressing bars (1"×0.21"×0.21") cut from wound dressing 2SM1114#1. Each bar was inoculated with 100 microliters of 0.5 MacFarlane inoculum. The *Staphylococcus aureus* was swabbed from a demonstrably active control culture. A control set of 4 bars with no *staphylococcus* was also included. Control samples with no gamma radiation treatment were kept in small sterile containers in heat sealed envelopes at room temperature and in the dark (see Table 12 for a summary of the controls).

TABLE 12

| Lot # | Control # | Pieces | Dosed | Gamma |
|---|---|---|---|---|
| OMLC_2SM114 | 61 | 4 | No | No |
| OMLC_2SM114 | 55 | 4 | No | No |
| OMLC_2SM114 | 65 | 4 | Yes | No |
| OMLC_2SM114 | 77 | 4 | Yes | No |
| OMLC_2SM114 | 74 | 4 | Yes | Yes |
| OMLC_2SM114 | 71 | 4 | Yes | Yes |
| OMLC_2SM114 | 58 | 4 | Yes | Yes |

The 46 irradiated wound dressing packages were opened under sterile conditions with sterile handling, an ethylene oxide sterile adhesive coated foam hacking (3M 9781 tape) was attached, a small off-cut piece (ca. 1.2"×0.2×0.12") of each wound dressing and backing was removed for individual wound dressing sterilization testing and the wound dressings were repackaged inside the original inner pack by heat sealing. 40 of these wound dressings were labeled with lot number and wound dressing number and sent out for evaluation. The off-cut and control pieces were given to the microbiology facility at St Vincent's PHS for sterility testing.

The off-cut pieces and control pieces were placed aseptically in labeled sample vessels (0.6" diam.×5") containing enriched thioglycolate growth media and incubated aerobically at 35° C. The culture media were examined at 7, 14 and 21 days for indications of growth. The samples were subcultured in Tryptic Soy Agar (TSA) with 5% sheep's blood, incubated at 35° C. and examined for growth after 48 hours.

The individual cultures were analyzed by turbidity testing and subculture swabbing. Absence of any growth in all the cultures and all the subcultures at 7, 14 and 21 days was demonstrated, even those cultures that were un-irradiated and dosed with *Staphylococcus aureus*. Gram positive staining of particular cultures confirmed these findings.

Example 5

Preparation of Sponge

Table 13 lists the hydrophilic polymers acquired for testing. Additional hydrophilic polymers include polylysine, chondroitan sulfate, starch and hyaluronan. Aqueous solutions (2.00% and 8.00% w/w) of ultrafiltered (Ametek) water and hydrophilic powder were prepared in clean, 1 liter bottles (Nalgene). Non-woven chitosan matting (PolyMed, Inc.) was converted into chitin non-woven matting by exposure to acetic anhydride (Aldrich 99%) over 48 hours at room temperature. Residual acetic anhydride was washed from the matting using multiple washings of ultrafiltered water. Exposure of the acetylated matting to NaOH (05 M) for 6 hours at room temperature hydrolyzed acetyl esters at the 3 and the 5 glucopyranose carbons without any hydrolysis of the acetyl amide at the carbon-2 position (verified by FTTR analyses). A twisted (1/cm) ultrafine (4 micron diameter) multi-filament (>50) polyester yarn (200 micron under 20 N load) was acquired (Multicraft Plastics, Portland, Oreg.).

TABLE 13

| Hydrophilic Polymer | Source | Specific Information |
|---|---|---|
| Chitosan | Primex (Iceland) | Food grade product, Degree of deacetylation >85%; Brookfield viscosity at 25° C., 1% aqueous solution, 1% acetic acid >300 cps; protein <0.2% |
| Carboxy methyl Cellulose | Aldrich | Catalogue # 419218 |
| Polyacrylic Acid | Aldrich | Catalogue #306215 |
| Alginic Acid | Aldrich | Catalogue #180947 |
| Dextran | Aldrich | Catalogue #D5501 |

Glacial acetic acid (Aldrich 99.99%) was added to the 2% and 8% chitosan aqueous solutions at 2% and 4% w/w of water respectively. Dissolution of the hydrophilic polymer solutions was achieved by slow axial rotation of the bottles at room temperature for up to 24 hours on a rotary bed stirrer. All the 2% solutions went readily into solution, with the highest viscosities measured by a LVT Brookfield viscometer at 25° C. and number 2 and number 3 spindles at less than 2000 cps. The 8% solutions of chitosan, alginic acid and acrylic acid had viscosities too high for measurement by the Brookfield viscometer. The very high viscosity fluid solutions in these instances prevented the solutions from being poured. Instead, the solutions were squeezed, pulled and scooped from their plastic bottles to load the molds. These latter very high viscosity fluids could not be readily processed in a manufacturing environment.

Sponges were formed by pouring/placing aqueous solutions into Teflon™-coated, 10.8 cm×10.8 cm×2.0 cm wells in aluminum molds to 1.7 cm deep in the case of 2% aqueous solutions or 0.45-0.70 cm deep in the case of 8% solutions. The solutions, initially at room temperature, were frozen into plaques by placement of the aluminum molds on cooling shelves at temperatures between −25° C. and −45° C. for 3 hours in laboratory (0.65 m$^2$) Virtis or (3.72 m$^2$ or 16.63 in$^2$) Hull freeze dryers. Sublimation of water from the plaques to produce hydrophilic polymeric sponges was accomplished by freeze-drying at less than 200 mTorr pressure, condenser at −80° C. with shelf temperature ramped slowly from −45° C. to 18° C. over 48 to 60 hours.

In the case of a sample of the 2% chitosan solutions, 4 strategies were tested to stop unwanted crust (top surface ice nucleation) formation in 2% chitosan solutions during freezing. One method was to place a thin polymer film over the top surface of the molds and in intimate wetting contact with the surface of the polymer solution prior to placement on the cold shelf for freezing. After the solution had been frozen into a plaque (ca. 1-2 hours), the thin protective polymer film is removed. Polyvinylidene chloride film (e.g., Saran™ wrap) is particularly useful, because its glass transition temperature is below −45° C. The thin film acts to stop dendritic ice formed on cold surfaces within the freezer/freeze dryer from depositing onto the top super-cooled hydrophilic polymer solution surface and nucleating a frozen surface crust. The second approach to prevent this crust layer was the use of an elevated (using 250 mm×6 mm×5 mm spacer bars) thin (e.g., 3 mm) acrylic plate place immediately above the mold. This had advantages over the thin film method, because it was not necessary to interrupt the freezing/freeze dryer cycle to remove the contacting thin protective polymer film. A third method, detailed in Example 7, used a permanent permeable chitin non-woven mat backing application on the top surface of the poured mold solutions. A fourth approach, detailed in example 11, was to use heat sealed, foil-lined pouches filled with hydrophilic solution as the solution containment during freezing.

At the completion of freeze drying (>48 hours), sponges were removed from the dryer, weighed and stored in heat sealed foil-lined pouches. The sponges were 10 cm×10 cm×1.7 cm in the case of solutions poured to 1.7 cm depth and 10 cm×10 cm×0.43 cm in the case of sponges poured to 0.45-0.7 cm depth. Moisture analysis using an Arizona Instruments Vapor Pro moisture analyser demonstrated % residual moisture at between 1% and 4% of sponge mass. Residual acetic acid in chitosan sponges was determined using a Mettler DL53 autotitrator and 0.0 10 M NaOH at between 27% and 22% sponge mass. Mean sponge densities for 2% and 8% solution chitosan sponges were 0.03 1±002 g/cm$^3$ and 0.103±0.014 g/cm$^3$ respectively. Mean sponge densities for the other hydrophilic sponges were 0.0248±0.0036 g/cm$^3$ for the 2% sponges and 0.0727±0.0023 g/cm$^3$ for the 8% sponges. The mean 29% density difference between chitosan sponges and the other hydrophilic sponges is caused predominantly by the acetic acid in the chitosan sponges and a small fraction of volatile component not taken into account when weighing the non chitosan sponges.

Figure 12A:
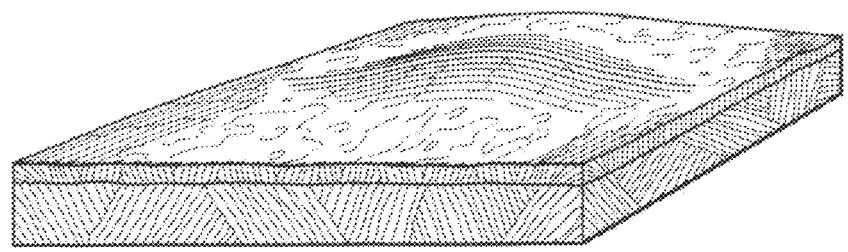
FIG. 12 shows a detailed drawing of typical chitosan sponge appearance.
Figure 12B:
Figure 12C:
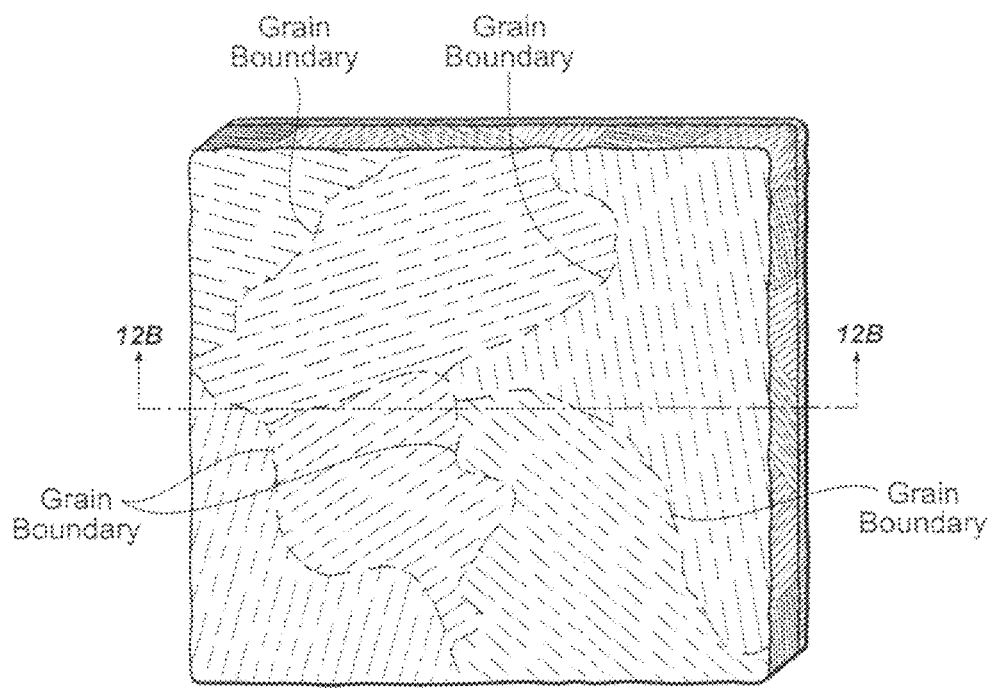

The 2% sponges from all the different hydrophilic test polymers were all well formed, compliant and of similar appearance and structure. All shrank by close to 8% in the width and length. The alginate and chitosan sponges had very good cohesive properties, resisting tearing and cracking with manipulation. The dextran, carboxy methyl cellulose and polyacrylic acid sponges were less cohesive, readily cracking and tearing with manipulation. The typical appearance of a 2% sponge frozen at close to −30° C. is shown in FIG. 12. The edges appeared smooth and decorated with a regular mosaic structural pattern. The top side of the sponge was slightly domed in its center. The only apparent feature was a regular 0.5 mm diameter×0.5 mm deep surface pocking. The base surface (i.e., the surface in contact with the Teflon™ mold base) exhibited a surface texture and apparent "large single crystal" regions separated by grain boundaries. A transverse cross-section cut using single sided safety razor blades (FIG. 13) demonstrates the internal structure. The grain boundaries in the base surface can be seen as boundaries demarcating regions of fine lamella oriented in different directions and likely originating from different heterogeneous nucleating events at the mold surface. The sponge internal structure can be described by a base layer of fine lamella (each 2-5 microns thick) that extends up into the sponge and encompasses close to 60% of the thickness of the sponge. Immediately above the base lamella is a thin interface (<10 microns) that separates the base fine layer from the top course layer This course layer originates from foreign dendritic ice contacting top surface solution when the top solution temperature falls below 0° C. The lamella in this layer are greater than 10 microns thick and are generally oriented vertical to the top surface. These coarse, vertical lamella resist compression normal to the plane of the sponge. The chitosan sponges formed by protecting the top surface from nucleation with dendritic ice did not have a top crust structure. These sponges had improved mechanical performance in terms of resistance to cracking, and improved compliance (flexibility) compared to sponges formed with no top surface protection.

All surfaces of the 2% sponges readily adsorbed blood or water All the uncompressed sponges were highly susceptible to collapse into a gel if they were contacted with excess water or blood for short periods of time (i.e., 5 seconds or greater).

The 8% sponges were considerably more rigid than the 2% sponges. Fine structure could not readily be observed in the sponge base, which appeared closed and smooth. These sponges did not adsorb blood and water as readily as the compressed 2% sponges. On cutting transverse sections of these sponges, it was observed that the internal structure was not unlike that in the 2% sponges: the course top vertical structure was present at close to the same relative depth as in the 2% sponge (i.e., 30-40%), and the base layer was composed of highly compact zones of lamella oriented near 30° from the normal and demarcated by fine grain boundaries.

Sponges from 2% solution were typically pressed by heating Teflon~ coated parallel plate platens to 80° C., and bringing the platens together to a constant spacer distance (typically 055 cm) at a constant rate of between 1200 mm/min to 5 mm/min. Sponge density of a 1.70 cm thick sponge pressed to 0.45 cm was approximately 0.10 g/cm$^3$. Sponges pressed at less than 80° C. and/or greater than 20 mm/min compression rate were susceptible to mechanical failure by cracking at grain boundaries and by brittle failure. This was found in the case of 2%, 1.7 cm thick chitosan sponges pressed at greater than 60 mm/min. Of 864 sponges, more than 260 sponges were discarded due to brittle collapse and failure. When the compression rate was adjusted to 20 mm/min there were only 43 discards from 864 sponges. When the compression rate was adjusted to 10 mm/min, there were less than 9 discards.

Figure 13A:
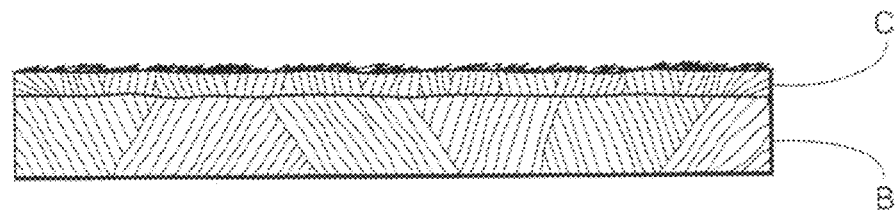
FIG. 13 shows the effect of compression on sponge internal structure as observed in sectioned typical 2% solution sponge compressed from 17 mm to 5 mm thick.
Figure 13B:
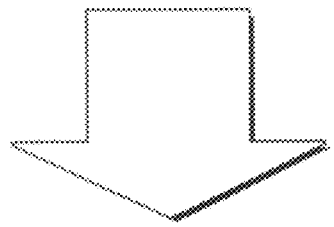
Figure 13B:
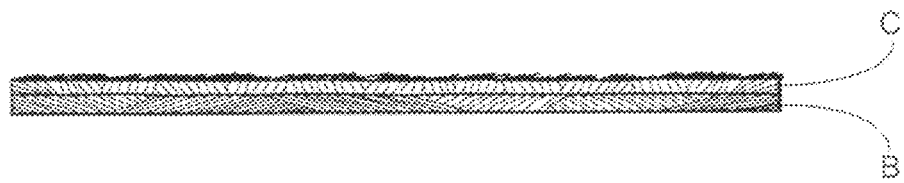

The change in sponge structure on pressing at slow rates (<12 mm/min) is shown in FIG. 13. It can be seen that the fine base lamella oriented at between 20° and 40° to the vertical are readily densified (75% compression) to a uniform base layer, while the vertical course top layer is only partially densified (ca. 55% compression). At slow compression rates, the grain boundary regions remain in intimate contact. At higher rates of compression (>20 mm/min), the grain boundary regions are more likely to separate.

Figure 14:
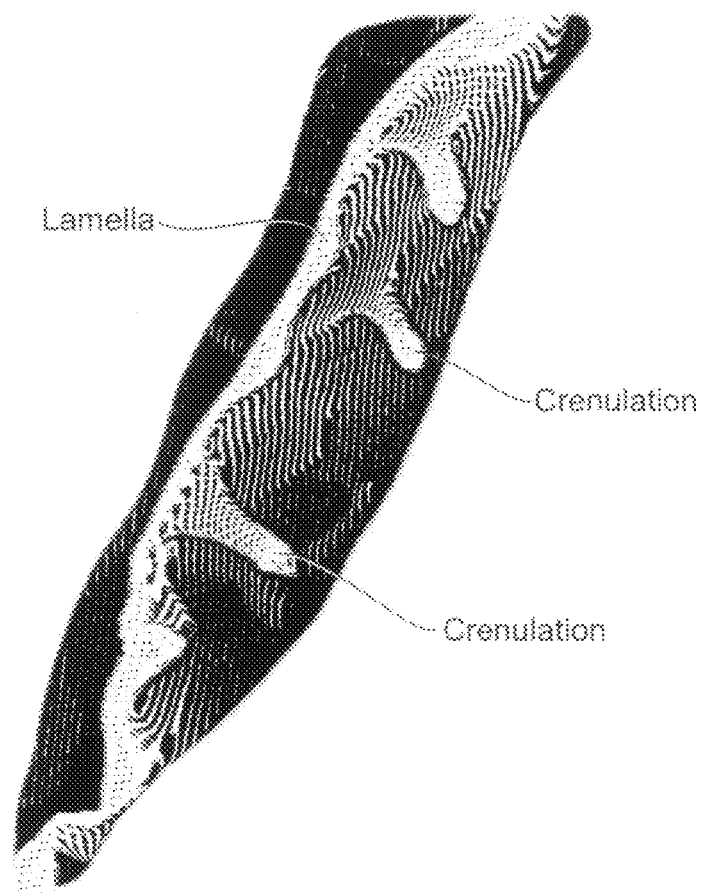
FIG. 14 shows a detailed drawing of single lamella showing surface crenulations.
Figure 15:
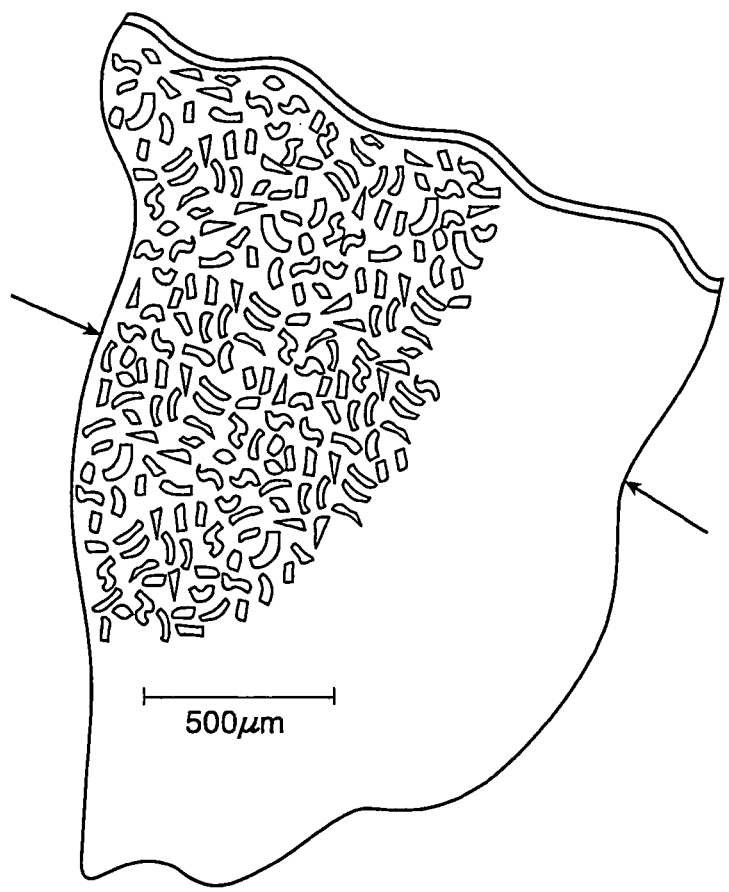
FIG. 15 shows a detailed drawing of a lamella surface.
Figure 16A:
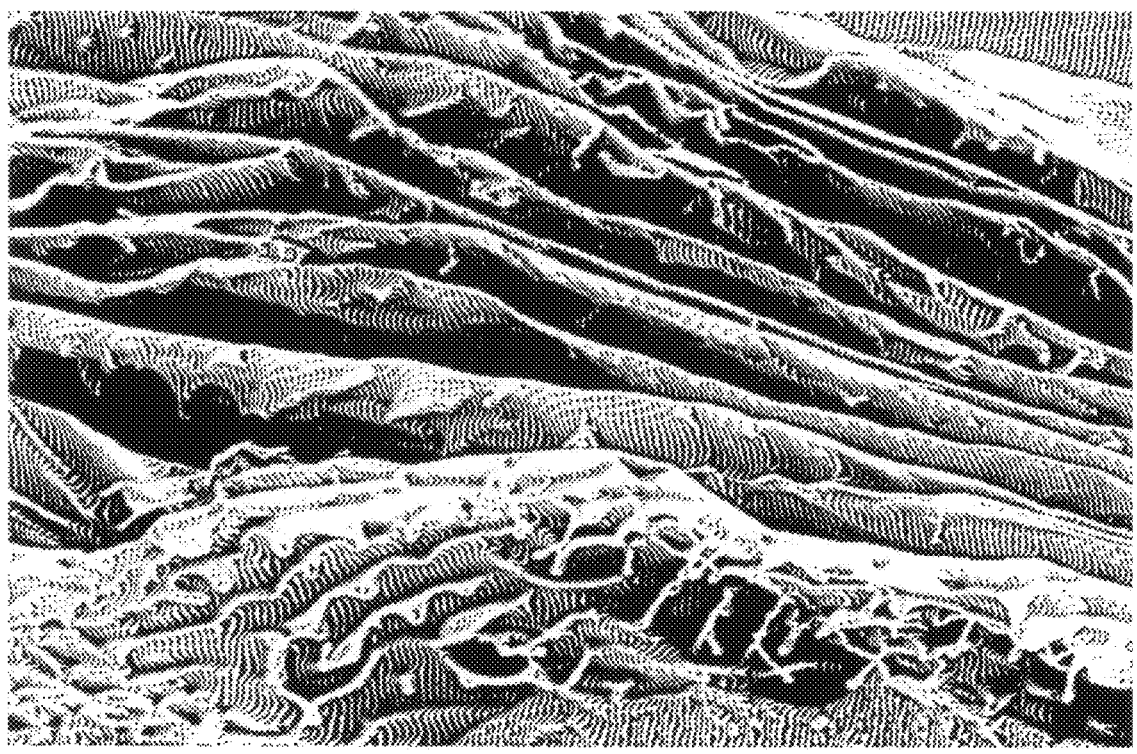
FIGS. 16(a)-16(g) shows the crenulations at various magnifications.
Figure 16B:
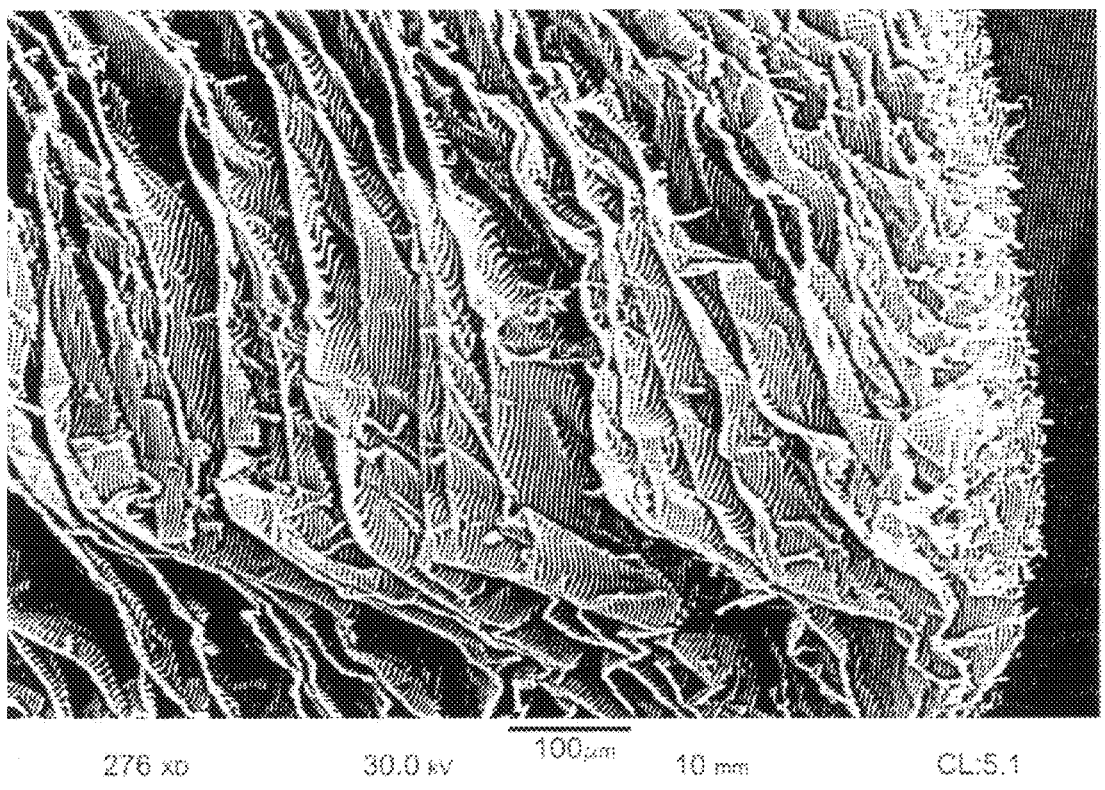
Figure 16C:
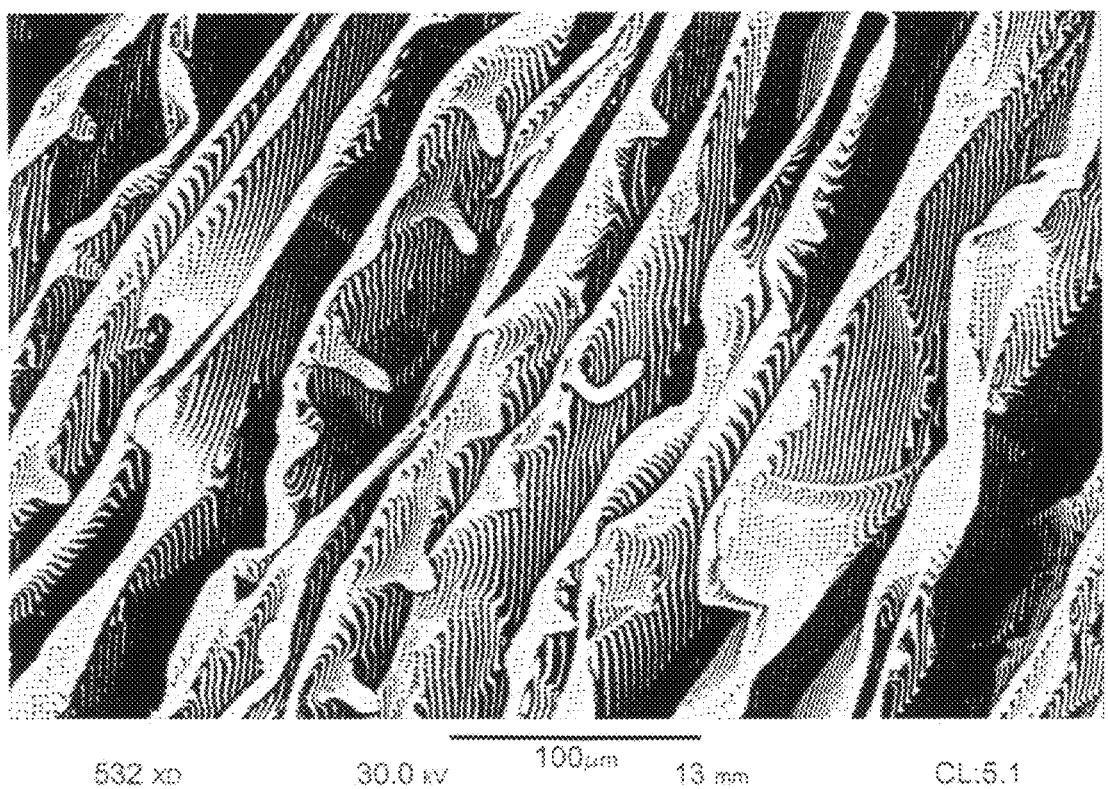
Figure 16D:
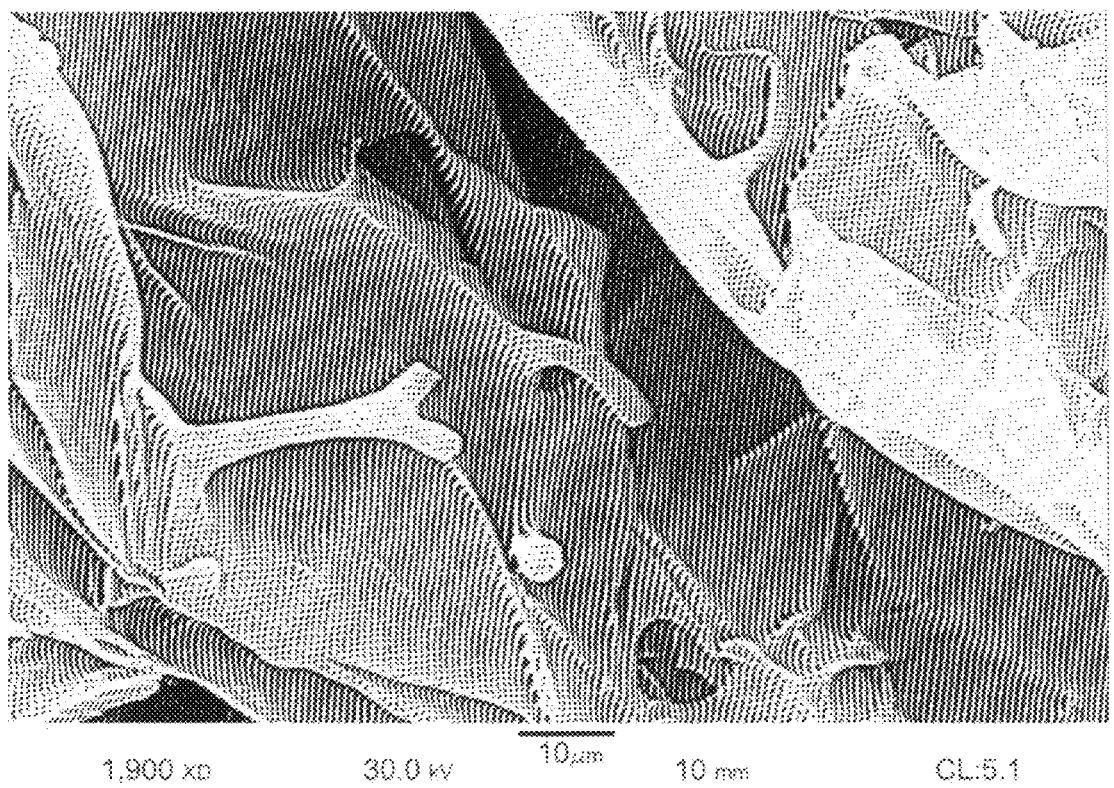
Figure 16E:
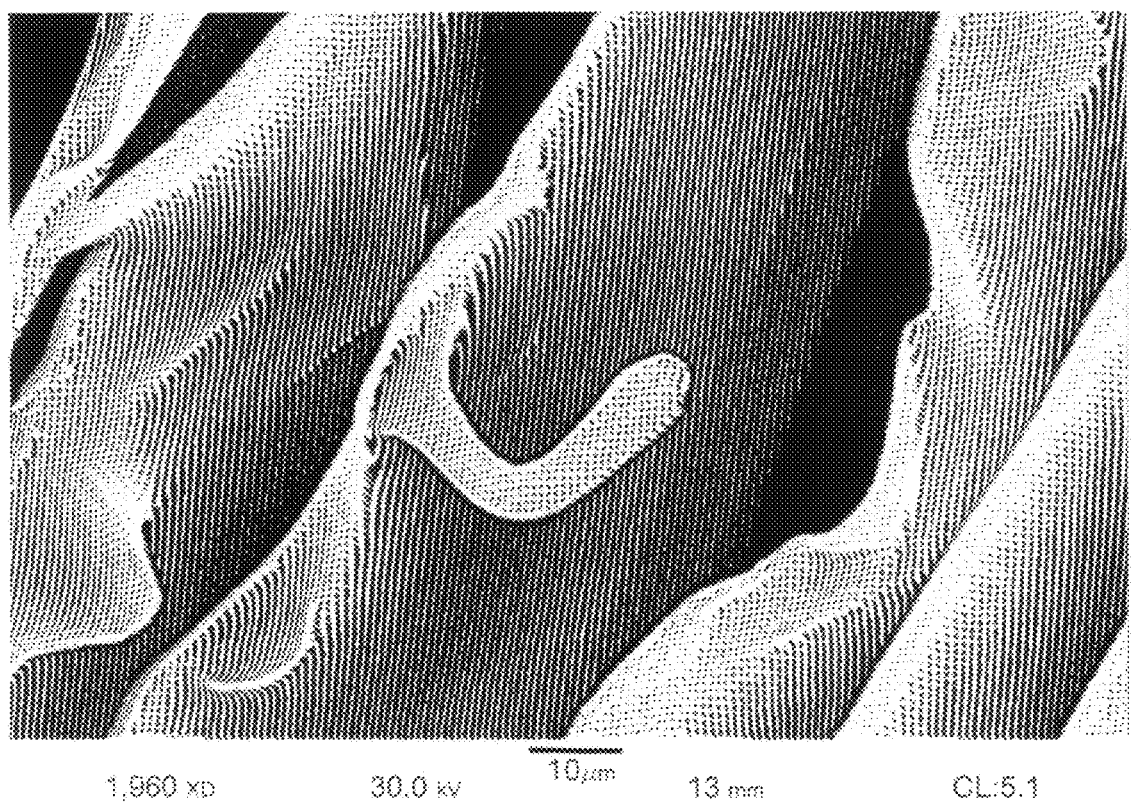
Figure 16F:
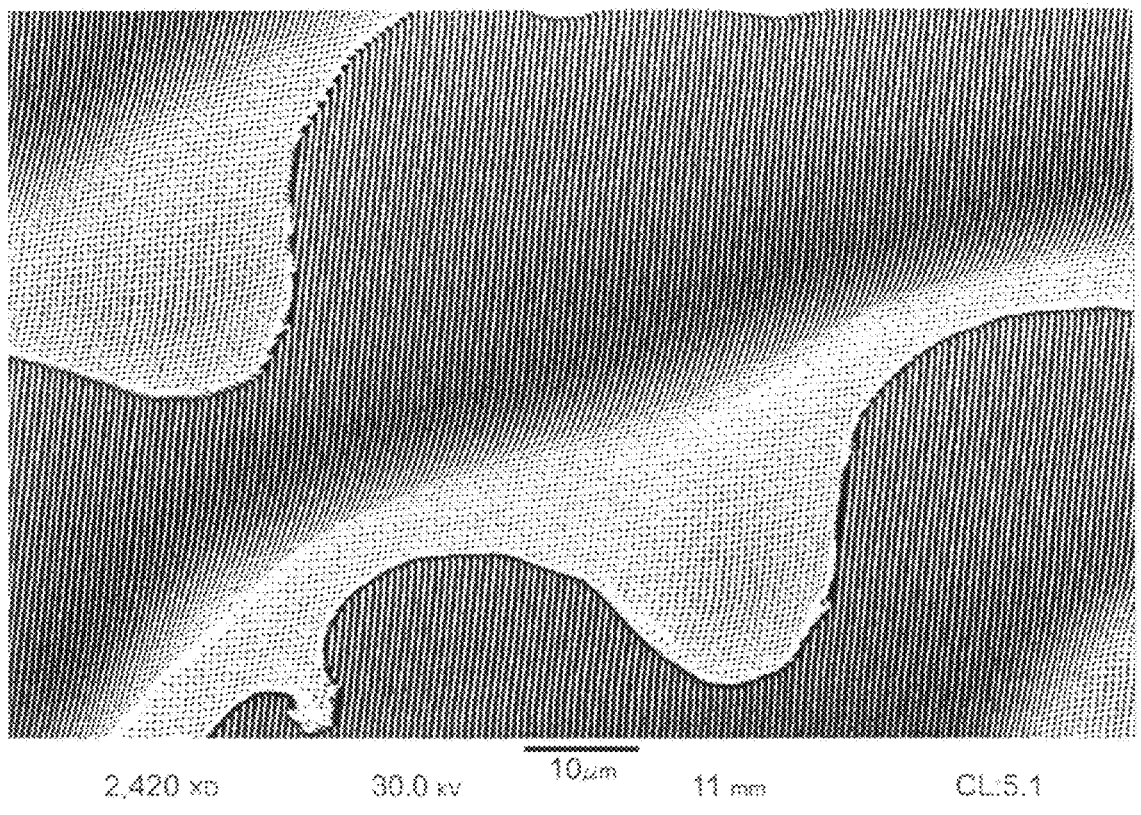
Figure 16G:
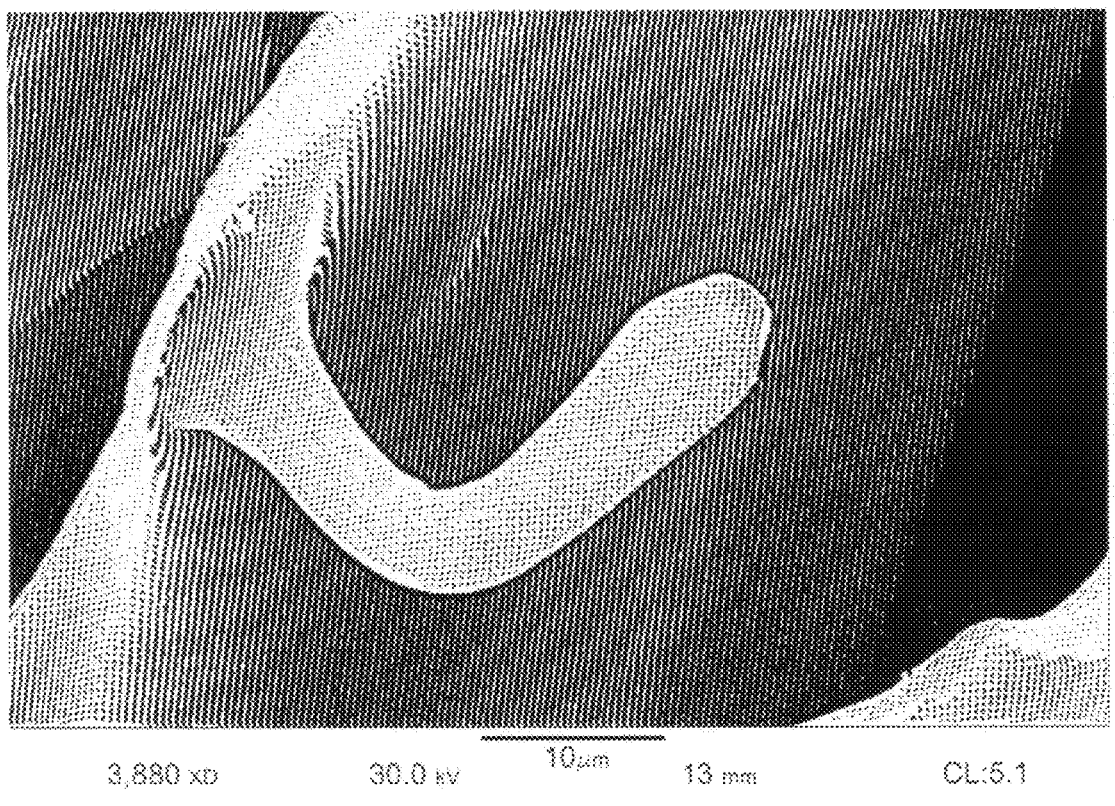
Figure 17:
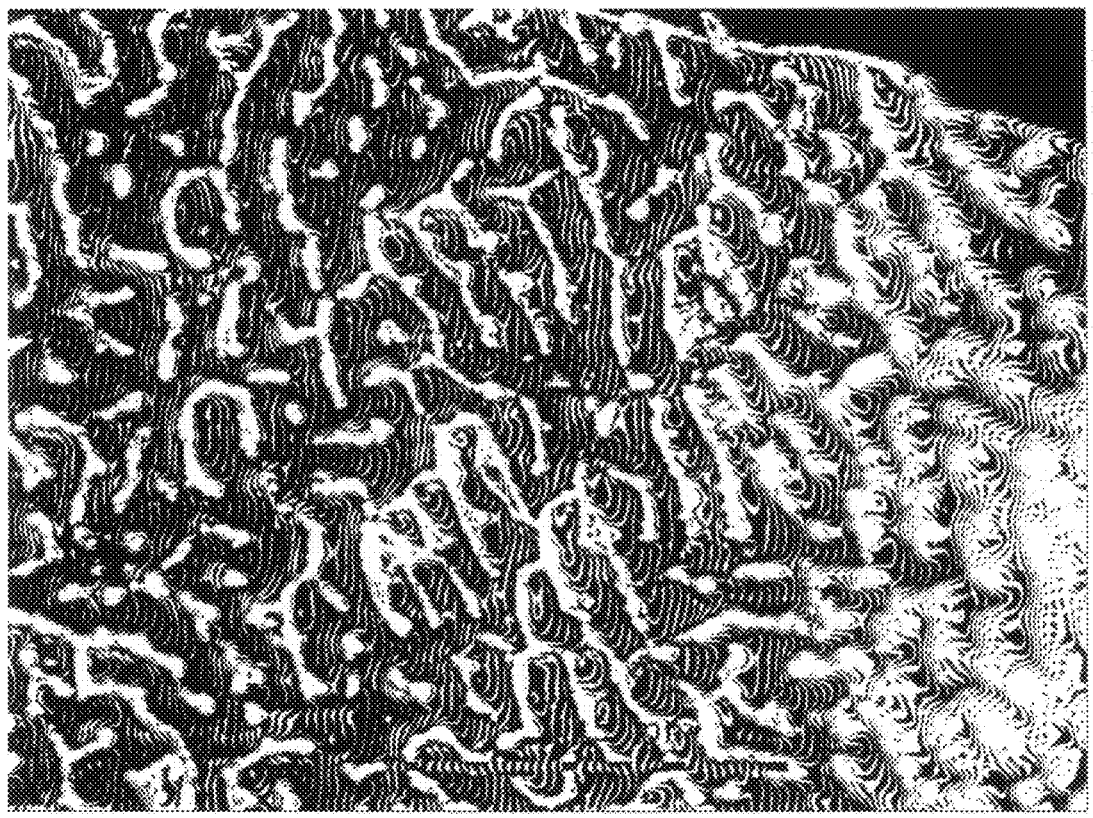
FIG. 17 shows a light microscope image with side lighting of single lamella removed from near the base of a chitosan sponge using micro-tweezers.

The (observation with respect to hydrophilic sponges) compressed sponges were less easily wetted by water or blood and they were more resistant to dissolution in both media. The compressed 2% sponges, although well wetted by blood did not dissolve. Adhesive strength of ~vetted compressed sponges was rated as PAA>Chitosan>CMC>Alginic acid. A very important determinant of an efficacious sponge is the presence of micron size crenulations (FIG. 14) orthonormal to the surface of the lamella. These crenulations protrude 3 to 10 microns from the lamella surface as small "teeth". Ideally they should be regularly distributed on at least one surface of the lamella. These structures are most common under controlled conditions when lamella are forming at orientations of lamella growth greater than 30° to the vertical. Also they appear to be controlled by an ability to rapidly cool the frozen plaque to less than −45° C. after the initial 30 to 60 minute period of freezing at −25° C. After pressing, test chitosan sponges were baked in a constant temperature convection oven at 80° C. for 30 minutes to anneal residual stresses and remove free acetic acid residue.

Example 6

Preparation of 2% Chitosan Sponges

A. Two samples of 2% chitosan sponges (N=3): one sample pressed from 1.7 cm to 0.55 cm at 20 mm/min while the other was not pressed. Both samples were baked at 80° C. for 30 minutes. Square test pieces (5 cm×5 cm) were cut from each sponge. A test piece was wetted with citrated porcine whole blood by 10 second submersion in blood at room temperature. It was attached centrally over a 4 mm diameter perforation in a 10 cm×10 cm surface of 12 mm thick, clear PVC (roughened using 400 grit wet and dry paper) by digital pressure (200-300 mmHg) for 3 minutes. Porcine whole blood at room temperature in a reservoir beneath the perforation was ramped in pressure (near 50 mmHg/s). A pressure transducer was attached to the reservoir to measure maximum pressure at failure.

Sponge test pieces (N=3) that were pressed held pressure to greater than 500 mmHg. Failure in these sponges was by loss of adhesive binding to the PVC. Sponge test pieces that had not been pressed (N=3) failed at less than 500 mmHg and failure was by sponge collapse and dissolution in the blood.

B. Two percent solution chitosan sponges (N=5) pressed from 1.7 cm to 0.55 cm at 10 mm/min; baked at 80° C. for 30 minutes; backed with foamed PVC tape and sterilized with gamma radiation (15 kGy). Test pieces (5 cm×5 cm) were submersed in porcine whole blood at room temperature for 10 seconds. The test piece was then attached centrally over a 4 mm diameter perforation on a flat PVC surface and held with loading pressure (near 600 mm Hg) for 3 minutes. At the end of this period, porcine whole blood at room temperature beneath the perforation was ramped to pressure (near 50 mmHg/s) to 300 mm Hg for 3 minutes and then again ramped at a similar rate until the attached test piece failed. Test piece failure occurred when the blood pressure was greater than 1800 mmHg. Failure was either by cohesive rupture, dissolution of top crust layer or adhesive loss of binding to the PVC.

C. A chitosan sponge test piece (4 cm×4 cm×0.5 cm) prepared from 8% solution was found to be effective at stopping bleeding in a 4 mm diameter acute swine aorta perforation (mean arterial blood pressure 70 mm Hg; bandage test piece hemostatic for longer than 30 minutes). 1-Jowever sponges from the 8% chitosan solution were inflexible and could not be readily conformed to a wound. On the other hand, sponges of the same density, formed from 2% solution chitosan solutions but pressed from 1.7 cm to 0.45 cm were not only effective at stopping the bleeding in this aorta perforation injury, but were also readily compliant and became more compliant with time when placed against the bleeding wound.

D. One inch diameter test pieces (N=12) from slow compressed (1.70 cm to 0.45 mm) initially 2% solution chitosan bandages formed from crust free sponges were attached (digital pressure for 3 minutes to initially free flowing bleeding, mean arterial pressure at 70 mmHg) to perforated (4 mm diameter) aortas in 12 anaesthetized swine. All test pieces staunched bleeding on the first application and were hemostatic over at least 30 minutes. In comparison, chitosan bandages formed from bandages with a crust layer (N>100) took on average 0.5 to 1.5 re-applications of pressure to staunch bleeding over the same time period.

E. Oval (3.8 cm×3.2 cm) test pieces (N=10) of fast pressed (>50 mm/min) 2% chitosan sponges were submersed in porcine whole blood at room temperature for 10 seconds. The test pieces were then attached centrally over a 4 mm diameter perforation on a flat PVC surface and held with digital pressure of 500 mm Jig for 3 minutes. At the end of this period, porcine whole blood at room temperature beneath the perforation was pressurized (at near 50 mmHg/s) to 300 mmHg/s for 3 minutes and then again ramped (at about 50 mmHg/s) until the test pieces failed. Failure was ranked in terms of maximum pressure attained, final adhesion to the test fixture, and bulk sponge cohesion after failure. This result was compared to the results of similar testing of 20 test pieces of 2% chitosan sponges that were slow pressed (compression rate <15 mm/min). The final burst and adhesion rankings were similar; however 60% of the fast pressed sponges had the lowest possible cohesion rankings due to gross crust dissolution and gelation while all 20 of the slow pressed bandages had the highest cohesion rankings.

F. Two sets of 2% chitosan sponges were prepared. One set had substantial lamella surface crenulations, another set had no crenulations on the lamella surfaces. Both sets of sponges were pressed at slow pressing rates to close to 0.10 g/cm$^3$ density. Sponges were baked at 80° C. for 30 minutes and backed with PVC foam film. In swine aorta perforation-experiments, the set of sponges with crenulated lamella were effective in staunching severe arterial bleeding in all cases (N=12). In sponges without crenulated lamella (N=6), no test pieces were effective in stanching bleeding.

Example 7

Preparation of Chitosan Sponge with Chitin Mesh Reinforcement

A chitin non-woven mesh soaked in water was placed against absorbent wipes (Kimwipe™) to reduce the amount of water in the non-woven chitin mat. The mat was cut to a 10 cm×10 cm square. It was then placed on the surface of a 2% chitosan solution that had been poured into a 10.8 cm×10.8 cm×2 cm deep aluminum mold well. It was observed that the mat remained suspended at the surface of the chitosan and that there was some adsorption of chitosan superficially into the mat. The chitosan solution and the mat were placed in the laboratory (Virtis) freeze dryer. The solution was frozen, and the water sublimed to reveal a sponge with a woven mat firmly attached at its surface. The sponge with the chitin matting dried at the same rate as a sponge with no chitin matting. A section of the chitin backed sponge was transverse cross-sectioned to reveal partial infiltration of the chitosan into the matting to close to 1.5 mm deep. However, the section also revealed that the top 1 mm of the mat surface was free of chitosan. The sponge with the chitin mat composite surface was pressed at 20 mm/min between parallel plate platens heated at 80±2° C. from 1.8 cm to 0.45 cm thickness. Transverse cross-sectioning through the sponge after pressing demonstrated that the interface between the chitin mat and the chitosan sponge had not been damaged by the pressing and that both mat and sponge were firmly fixed together. Also the presence of the chitin mat had stopped the formation of sponge crust (course ice nucleation from the top surface down) that can affect sponge compliance and sponge resistance to dissolution. The sponge was tested in an acute swine 4 mm diameter aortic perforation model. Bleeding in this injury was not being stopped by regular chitosan bandage pieces and the chitin mat backed test piece was applied by holding digital pressure for 3 minutes. The surgeon applying the 2.5 cm diameter test piece noted that the test piece was particularly compliant and that be could remove his finger without it sticking to the chitin backing. The test piece sealed the injury site for more than the required 30 minute test period of the protocol. It remained well adhered to the injury site and showed no signs of dissolution even though it did not have the protective impermeable backing normally applied with this bandage. Also, it was observed that the bandage was compliant on the injury as it was possible to observe a pulse through the flexing of the bandage.

Example 8

Chitosan Impregnated Thread

The 0.5 mm diameter polyester multifilament submerged in 2% chitosan solution expanded to ca. 2 mm in diameter. The chitosan soaked thread at room temperature was then gently rested on a flat hydrophobic Teflon coated aluminum tray without drawing any of the solution out of the expanded thread. The tray was then placed on the Virtis Freeze dryer shelf at −25° C. and allowed to freeze. The ice was removed from the thread by freeze drying leaving a 2 mm diameter expanded thread impregnated with chitosan sponge at 0.033 g/cm$^3$. Application of a tensile force of close to 10 N to the expanded thread and pressure of about 500 mmHg normal to the thread surface through a tapered nitrile rubber, non-stick pinching die compressed the thread diameter from 2 mm to about 0.7 mm. The thread exhibited good compliance and was prepared for weaving into a gauze-like dressing. A portion of the thread was baked at 80° C. for 10 minutes. It was then submersed in blood for 10 seconds and held firmly against a clean test PVC surface for 3 minutes. It demonstrated good adhesion.

Example 9

Comparative Flexure Between Compressed Low Density Sponges and Non-Pressed High Density Sponges The method of densification presented here reduces a highly compliant low density interconnected sponges in volume by a controlled reduction in thickness, width and/or radius. Preferably, the compliance of the hydrophilic polymers is not modified with plasticizers such as glutamic acid or glycerol, because this modification renders the sponges more susceptible to dissolution and sponge collapse under severe bleeding. This example shows that compression of low density sponges to higher density sponges results in sponges of lower elastic modulus than if the sponge of the chemically identical higher density had been formed without densification.

In order to determine elastic modulus (F), deflections from the horizontal were determined in single, cantilever beam experiments. Rectangular beams were cut from pressed 2% sponges and non-pressed 8% sponges. The beams were 9 cm long, and 2.54 cm wide. They were anchored so that only 6.7 cm of the beam extended from the edge of a flat horizontal surface. A 20 g or 30 g weight was placed on the beam tip at 6.5 cm from the anchor point. The deflection of the 6.5 cm point of the beam normal from the horizontal was measured 3 seconds after loading. Elastic modulus (E) was determined from the equation:

$$E = P \cdot L^3 / (3 y \cdot I)$$

where $I = w \cdot h^3 / 12$

P=load (N); L free beam length (m); y=beam deflection from the horizontal (m); w beam width (m); h=beam height in the vertical plane (m); I=moment of inertia (m4)

The thickness of the beam was determined using a digital caliper. After determination of beam deflection, the beam was cut into 2.54 cm×2.54 cm squares, weighed and density determined. The results of the testing are shown in Table 2. It can be seen that the 8% samples are all more resistant to flexure than the 2% samples. The mean elastic moduli (MPa) for compressed 2% sponges are 6.43±3.3, 1.75, 3.5 and 2.9±0.4 for chitosan, polyacrylic acid, carboxy methyl cellulose and alginic acid respectively. The mean elastic moduli (MPa) for 8% sponges are 10.6±3.3, 12.4, 4.54 and 5.7±2.1 for chitosan, polyacrylic acid, carboxy methyl cellulose and alginic acid respectively. The ratio of mean elastic moduli of pressed 2% sponges over 8% sponges is 0.61, 0.14, 0.77 and 0.51 for chitosan, polyacrylic acid, carboxy methyl cellulose and alginic acid respectively.

TABLE 14

| Polymer | % Soln | Test # | Sponge density g/cm$^3$ | Beam Deflection (mm) | Mass Loaded (g) | Beam thickness (mm) | Elastic Modulus (MPa) |
|---|---|---|---|---|---|---|---|
| Chitosan | 2 | 1 | .096 | 9 | 30 | 5.45 | 8.73 |
| | 2 | 2 | 0.107 | 8 | 30 | 5.45 | 9.83 |
| | 2 | 3 | 0.094 | 23 | 30 | 5.45 | 3.42 |
| | 2 | 4 | 0.090 | 21 | 30 | 5.45 | 3.74 |
| | 8 | 1 | 0.093 | 5 | 30 | 7.1 | 6.82 |
| | 8 | 2 | 0.093 | 2 | 30 | 8.5 | 10.36 |
| | 8 | 3 | 0.092 | 1.5 | 30 | 8.4 | 14.31 |
| | 8 | 4 | 0.115 | 1.5 | 30 | 8.6 | 13.34 |
| | 8 | 5 | 0.121 | 2.5 | 30 | 8.6 | 8.00 |
| PAA | 2 | 1 | 0.071 | 30 | 20 | 5.45 | 1.75 |
| | 8 | 1 | 0.071 | 2 | 20 | 7.0 | 12.37 |
| CMC | 2 | 1 | 0.079 | 15 | 20 | 5.45 | 3.49 |
| | 2 | 2 | 0.086 | 15 | 20 | 5.45 | 3.49 |
| | 8 | 1 | 0.074 | 10 | 20 | 6.1 | 3.74 |
| | 8 | 2 | 0.076 | 7 | 20 | 6.1 | 5.34 |

TABLE 14-continued

| Polymer | % Soln | Test # | Sponge density g/cm³ | Beam Deflection (mm) | Mass Loaded (g) | Beam thickness (mm) | Elastic Modulus (MPa) |
|---|---|---|---|---|---|---|---|
| AA | 2 | 1 | 0.078 | 15 | 20 | 5.6 | 3.22 |
|  | 2 | 2 | 0.077 | 15 | 20 | 5.7 | 3.05 |
|  | 2 | 3 | 0.074 | 20 | 20 | 5.6 | 2.42 |
|  | 8 | 1 | 0.071 | 6 | 20 | 5.6 | 8.05 |
|  | 8 | 2 | 0.074 | 7 | 20 | 6.3 | 4.85 |
|  | 8 | 3 | 0.070 | 7 | 20 | 6.6 | 4.22 |

PAA = polyacrylic acid, CMC = carboxy methyl cellulose, AA = alginic acid

Example 10

Pressed two percent solution, composite polyacrylic acid sponges (N=2) test pieces (5 cm×5 cm) were submersed in porcine whole blood at room temperature for 10 seconds. The test piece was then attached centrally over a 4 mm diameter perforation on a flat PVC surface and held with loading pressure (750 mmHg) for 3 minutes. At the end of this period, porcine whole blood at room temperature beneath the perforation was ramped to pressure (near 50 mmHg/s) to 300 mmHg for 3 minutes and then again ramped at a similar rate until the attached test piece failed. Test piece failure occurred when the blood pressure was greater than 2300 mmHg. Failure was by sponge cohesive rupture.

Example 11

An approach to achieve very good thermal contact with freezing shelves, stop course crust formation during freezing and to apply a controlled level of shear normal to growing vertical lamella is described. 1-Teat sealed, foil-lined pouches (15 cm×23 cm) were filled with 200 g of 2% chitosan solution. All air was removed from the pouch prior to final sealing. The pouches were placed in a laboratory Virtis freeze dryer between parallel plate shelves at −25° C. to freeze for at least 180 minutes. The Virtis dryer had a "stoppering" facility which enabled the upper shelf to be brought down onto the lower shelf and hence to firmly contact and apply a loading to the chitosan filled, foil pouches placed between spacers on the lower shelf The pouches were filled to a level such that when the upper shelf was lowered onto the bottom one, the upper shelf rested firmly on the top surface of the solution filled pouch. The extent of pressure on the pouch could be controlled by the free weight of the top shelf and by the number of pouches resting between the two shelves. In this example, 1.7 cm spacer bars were used, only 2 pouches were placed between shelves and the load on the pouches was close to 10 kg. Prior to freeze drying, the stoppered shelves were raised; the frozen plaques removed from their pouches and placed on the cold freeze dryer shelves. Expansion inside the pouches on freezing was accommodated by partial internal rending of the heat seal. The plaques were subsequently freeze dried into sponges. Transverse sectioning through the sponges demonstrated uniform lamella structure growing from top and bottom surfaces and meeting in the middle of the sponges. The top structure was the mirror image of the bottom structure. The lamella were all uniformly oriented at between 20° and 30° to the vertical and in the direction away from the center to the edge of the sponge. The sponges demonstrated an absence of grain boundaries. The sponges were pressed from 1.7 cm thickness to 0.55 cm. They had excellent mechanical properties in terms of tensile strength, compliance and resisting to tearing or fracturing on severe bending. The sponges were baked, hacked with PVC foam backing and gamma irradiated at 15 kGy. A single oval test piece was applied to an aorta perforation in the acute swine model. This was effective in stopping arterial bleeding over the 30 minute test period. The surgeon noted that the sample had very good compliance.

Example 12

A simple positive textured surface was created on a 10 cm×10 cm×1.7 cm chitosan sponge. This was achieved using a negative patterned 10 cm×10 cm×0.25 cm aluminum card. The pattern was made by running a 400 grit wet and dry paper over the flat aluminum surface. This surface was coated with a non-permanent red dye most of which was removed from the top portion of the surface by wiping with a dry cloth. A chitosan sponge compressed against this surface demonstrated the positive surface patterning as that revealed by the red dye in the aluminum card.

All references discussed above are herein incorporated by reference in their entirety for all purposes. While this invention has been particularly shown and described with references to preferred embodiments thereof, it will be understood by those skilled in the art that various changes in form and details may be made therein without departing from the spirit and scope of the invention as defined by the appended claims.

We claim:

1. A method comprising
    compressing a structure comprising a freeze-dried chitosan biomaterial at a rate of less than 20 mm/min by application of mechanical pressure and heat,
    providing a wound dressing comprising the freeze-dried and heat-compressed structure having a density, after being heat-compressed, of between about 0.14 g/cm³ to about 0.6 g/cm³, and a moisture content between about 2% and 5% w/w,
    inserting the freeze-dried and heat-compressed structure into a wound site into contact with tissue for hemorrhage control to form a chitosan adhesive material in combination with the blood flowing, and
    adhering the freeze-dried and heat-compressed structure to tissue in the presence of blood flow, wherein the structure has a degree of adhesion to the wound site of about 40 kPa to about 500 kPa, and
    staunching bleeding within the wound site.

2. A method according to claim 1
    wherein the freeze-dried and heat-compressed structure includes a backing support material.

3. A method according to claim 1
    wherein inserting includes conforming the freeze-dried and heat-compressed structure into a configuration of the wound site.

4. A method according to claim 1
    wherein inserting includes applying pressure to the freeze-dried and heat-compressed structure.

5. A method comprising
compressing a structure comprising a freeze-dried chitosan biomaterial at a rate of less than 20 mm/min by application of mechanical pressure and heat,
providing a wound dressing comprising the freeze-dried and heat-compressed structure having a density, after being heat-compressed, of between about 0.14 g/cm$^3$ to about 0.6 g/cm$^3$, and a moisture content between about 2% and 5% w/w, wherein the freeze-dried and heat-compressed structure includes a collagen-free backing support material,
inserting the freeze-dried and heat-compressed structure into a wound site into contact with tissue for hemorrhage control to form a chitosan adhesive material in combination with the blood flowing, and
adhering the freeze-dried and heat-compressed structure to tissue in the presence of blood flow, wherein the structure contains pores with pore diameters of about 15 microns to about 300 microns and has a degree of adhesion to the wound site of about 40 kPa to about 500 kPa, and
staunching bleeding within the wound site.

6. A method according to claim 5
wherein inserting includes conforming the freeze-dried and heat-compressed structure into a configuration of the wound site.

7. A method according to claim 5
wherein inserting includes applying pressure to the freeze-dried and heat-compressed structure.

8. A method comprising
compressing a structure comprising a freeze-dried chitosan biomaterial at a rate of less than 20 mm/min by application of mechanical pressure and heat,
providing a wound dressing comprising e the freeze-dried and heat-compressed structure having a density, after being heat-compressed, of between about 0.14 g/cm$^3$ to about 0.6 g/cm$^3$, and a moisture content between about 2% and 5% w/w, said freeze-dried and heat-compressed structure consisting of chitosan and one or more of alginate, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan, an active ingredient, or another wettable polymer,
inserting the freeze-dried and heat-compressed structure into a wound site into contact with tissue for hemorrhage control to form a chitosan adhesive material in combination with the blood flowing, and
adhering the freeze-dried and heat-compressed structure to tissue in the presence of blood flow, wherein the structure has a degree of adhesion to the wound site of about 40 kPa to about 500 kPa, and
staunching bleeding within the wound site.

9. A method according to claim 8
wherein the freeze-dried and heat-compressed structure includes a backing support material.

10. A method according to claim 8
wherein inserting includes conforming the freeze-dried and heat-compressed structure into a configuration of the wound site.

11. A method according to claim 8
wherein inserting includes applying pressure to the freeze-dried and heat-compressed structure.

12. A method according to claim 1 further comprising compressing the structure comprising a freeze-dried chitosan biomaterial at a rate of less than 12 mm/min by application of mechanical pressure and heat.

13. A method according to claim 1 further comprising adding an active ingredient to the freeze-dried and heat-compressed structure selected from the group comprising calcium, thrombin, factor VIIa, factor XIII, thromboxane A2, prostaglandin-2a, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibroblast growth factor, keratinocyte growth factor, nerve growth factor, penicillin, ampicillin, methicillin, amoxycillin, clavamox, clavulanic acid, amoxicillin, aztreonam, imipenem, streptomycin, Kanamycin, Tobramycin, gentamicin, vancomycin, clindamycin, erythroniycin, polymyxin, bacitracin, amphotericin, nystatin, rifampicin, tetracycline, doxycycline, chloramphenicol and combinations thereof.

14. A method according to claim 1, wherein the freeze-dried and heat-compressed structure further comprises a wettable polymer selected from the group consisting of a chitin, an alginate, a neutralized chitosan, a reacetylated chitosan, a poly(glycolic acid), a poly(lactic acid), a poly(e-caprolactone), a poly(13-hydroxybutyric acid), a poly(13-hydroxyvaleric acid), a polydioxanone, a poly(ethylene oxide), a poly(malic acid), a poly(tartronic acid), a polyphosphazene, a polyethylene, a polypropylene, a metallocene polymer, a polyurethane, a polyvinylchloride polymer, a polyester, a polyamide and combinations thereof.

15. A method according to claim 5 further comprising compressing the structure comprising a freeze-dried chitosan biomaterial at a rate of less than 12 mm/min by application of mechanical pressure and heat.

16. A method according to claim 5 further comprising adding an active ingredient to the freeze-dried and heat-compressed structure selected from the group comprising calcium, thrombin, factor VIIa, factor XIII, thromboxane A2, prostaglandin-2a, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibroblast growth factor, keratinocyte growth factor, nerve growth factor, penicillin, ampicillin, methicillin, amoxycillin, clavamox, clavulanic acid, amoxicillin, aztreonam, imipenem, streptomycin, Kanamycin, Tobramycin, gentamicin, vancomycin, clindamycin, erythroniycin, polymyxin, bacitracin, amphotericin, nystatin, rifampicin, tetracycline, doxycycline, chloramphenicol and combinations thereof.

17. A method according to claim 8 further comprising compressing the structure comprising a freeze-dried chitosan biomaterial at a rate of less than 12 mm/min by application of mechanical pressure and heat.

18. A method according to claim 8 wherein the active ingredient is selected from the group consisting of calcium, thrombin, factor VIIa, factor XIII, thromboxane A2, prostaglandin-2a, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibroblast growth factor, keratinocyte growth factor, nerve growth factor, penicillin, ampicillin, methicillin, amoxycillin, clavamox, clavulanic acid, amoxicillin, aztreonam, imipenem, streptomycin, Kanamycin, Tobramycin, gentamicin, vancomycin, clindamycin, erythroniycin, polymyxin, bacitracin, amphotericin, nystatin, rifampicin, tetracycline, doxycycline, chloramphenicol and combinations thereof.

19. A method according to claim 8 wherein the wettable polymer is selected from the group consisting of a chitin, a neutralized chitosan, a reacetylated chitosan, a poly(glycolic acid), a poly(lactic acid), a poly(e-caprolactone), a poly(13- hydroxybutyric acid), a poly(13-hydroxyvaleric acid), a polydioxanone, a poly(ethylene oxide), a poly(malic acid), a poly(tartronic acid), a polyphosphazene, a polyethylene, a polypropylene, a metallocene polymer, a polyurethane, a polyvinylchloride polymer, a polyester, a polyamide and combinations thereof.

* * * * *